US006184231B1

(12) United States Patent
Hewawasam et al.

(10) Patent No.: US 6,184,231 B1
(45) Date of Patent: Feb. 6, 2001

(54) 3-SUBSTITUTED-4-ARYLQUINOLIN-2-ONE DERIVATIVES AS POTASSIUM CHANNEL MODULATORS

(75) Inventors: Piyasena Hewawasam; John E. Starrett, Jr., both of Middletown, CT (US)

(73) Assignee: Bristol-Myers Squibb, Princeton, NJ (US)

( * ) Notice: Under 35 U.S.C. 154(b), the term of this patent shall be extended for 0 days.

(21) Appl. No.: 09/452,523

(22) Filed: Dec. 1, 1999

Related U.S. Application Data
(60) Provisional application No. 60/111,079, filed on Dec. 4, 1998.

(51) Int. Cl.[7] .................. A61K 31/4704; C07D 215/227
(52) U.S. Cl. ........................... 514/312; 546/157; 546/156
(58) Field of Search ............................. 514/312; 546/157, 546/156

(56) References Cited

U.S. PATENT DOCUMENTS

| | | |
|---|---|---|
| 5,200,422 | 4/1993 | Olesen et al. . |
| 5,565,472 | 10/1996 | Hamanaka . |
| 5,565,483 | 10/1996 | Hewawasam et al. . |
| 5,892,045 | 4/1999 | Sit et al. . |
| 5,972,961 | * 10/1999 | Hewawasam ........................ 514/312 |

FOREIGN PATENT DOCUMENTS

| | | |
|---|---|---|
| 477-819 | 4/1992 | (EP) . |
| WO 93/08800 | 5/1993 | (WO) . |
| WO 98/23273 | 6/1998 | (WO) . |
| WO 99/09983 | 3/1999 | (WO) . |

OTHER PUBLICATIONS

Ahmed, F. et al., "Some Features of the Spasmogenic Actions of Acetylcholine and Histamine in Guinea–Pig Isolated Trachealis", *Br. J. Pharmacol.*, 83, p. 227–233 (1984).

Baró, I. and Escande, D., "A $Ca^{2+}$–activated $K^+$ Current in Guinea–pig Atrial Myocytes", *Pflügers Archiv.*, 414 (Suppl. 1), p. S168 (1989).

Cook, N.S., "The Pharmacology of Potassium Channels and Their Therapeutic Potential", *Trends in Pharmacol. Sciences*, 9, p. 21–28 (Jan., 1988).

Koh, D–S., et al., "Effect of the Flavoid Phloretin on $Ca^{2+}$–activated $K^+$Channels in Myelinated Nerve Fibres of Xenopus Laevis", *Neuroscience Lett.* 165, p. 167–170 (1994).

Laurent, F., et al., "Evaluation of the relaxant effects of SCA40, a novel charybdotoxin–sensitive potassium channel opener, in guinea–pig isolated trachealis", *Br. J. Pharmacol.*, 108, 622–626 (1993).

Olesen, S.–P., et al., "Selective activation of $Ca^{2+}$–dependent $K^+$channels by novel benzimidazolone", *European J. Pharmacol.*, 251, p. 53–59 1994.

Quast, U. and Cook, N. S., "Moving Together: $K^+$Channel Openers and ATP–sensitive $K^+$Channels", *Trends in Pharmacol. Sciences*, 10, p. 431–435 Nov., 1989.

Singer, J.J. and Walsh, J.V., "Characterization of Calcuim–activated Potassium Channels in Single Smooth Muscle Cells Using the Patch–clamp Technique", *Pflügers Archiv.*, 408, p. 98–111 (1987).

Paramasivam K and Shanmugam P. Indian J. Chem., Sect. B, 23B(4), 311–15, 1984.*

* cited by examiner

Primary Examiner—Evelyn Mei Huang
(74) Attorney, Agent, or Firm—Aldo A. Algieri

(57) ABSTRACT

The present invention provides novel 3-substituted-4-arylquinolin-2-one derivatives having the general formula

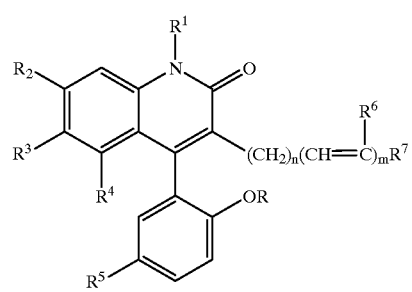

I wherein R, $R^1$, $R^2$, $R^3$, $R^4$, $R^5$, $R^6$ and $R^7$ are as defined herein, or a non-toxic pharmaceutically acceptable salt thereof which are modulators of the large conductance calcium-activated $K^+$ channels and are useful in the treatment of disorders which are responsive to the opening of the potassium channels.

14 Claims, No Drawings

3-SUBSTITUTED-4-ARYLQUINOLIN-2-ONE DERIVATIVES AS POTASSIUM CHANNEL MODULATORS

CROSS-REFERENCE TO RELATED APPLICATION

This is a nonprovisional application which claims the benefit of provisional applications U.S. Ser. No. 60/111,079, filed Dec. 4, 1998.

FIELD OF THE INVENTION

The present invention is directed to novel 3-substituted-4-arylquinolin-2-one derivatives which are modulators of the large-conductance calcium-activated potassium (BK) channels and, therefore, useful in the protection of neuronal cells and diseases arising from dysfunction of cellular membrane polarization and conductance. The present invention also provides a method of treatment with the novel substituted quinolin-2-one derivatives and to pharmaceutical compositions thereof.

BACKGROUND OF THE INVENTION

Potassium channels play a key role in regulation of cell membrane potential and modulation of cell excitability. Potassium channels are largely regulated by voltage, cell metabolism, calcium and receptor mediated processes. [Cook, N. S., *Trends in Pharmacol. Sciences* (1988), 9, 21; and Quast, U., et al., *Trends in Pharmacol. Sciences* (1989), 10, 431]. Calcium-activated potassium ($K_{ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. Large-conductance calcium-activated potassium (Maxi-K or BK) channels are present in many excitable cells including neurons, cardiac cells and various types of smooth muscle cells. [Singer, J. et al., *Pflugers Archiv.* (1987) 408,98; Baro, I., et al., *Pflugers Archiv.* (1989) 414 (Suppl. 1), S168; and Ahmed, F. et al., *Br. J. Pharmacol.* (1984) 83, 227].

Potassium ions play a dominant role in controlling the resting membrane potential in most excitable cells and maintain the transmembrane voltage near the $K^+$ equilibrium potential ($E_k$) of about −90 mV. It has been shown that opening of potassium channels shift the cell membrane potential towards the equilibrium potassium membrane potential ($E_k$), resulting in hyperpolarization of the cell. [Cook, N. S., *Trends in Pharmacol. Sciences* (1988), 9, 21]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells.

A range of synthetic and naturally occurring compounds with BK opening activity have been reported. The avena pyrone extracted from avena sativa-common oats has been identified as a BK channel opener using lipid bi-layer technique [International Patent application WO 93/08800, published May 13, 1993]. 6-Bromo-8-(methylamino)imidazo[1,2-a]pyrazine-2-carbonitrile (SCA-40) has been described as a BK channel opener with very limited electrophysiological experiments [Laurent, F. et al., *Br. J. Pharmacol.* (1993) 108, 622–626]. The flavanoid, Phloretin has been found to increase the open probability of $Ca^{2+}$-activated potassium channels in myelinated nerve fibers of *Xenopus laevis* using outside-out patches [Koh, D-S., et al., *Neuroscience Lett.* (1994) 165, 167–170].

In European patent application EP-477,819 published Jan. 4, 1992 and corresponding U.S. Pat. No. 5,200,422, issued Apr. 6, 1993 to Olesen, et al., a number of benzimidazole derivatives were disclosed as openers of BK channels by using single-channel and whole-cell patch-clamp experiments in aortic smooth muscle cells. Further work was reported by Olesen, et al., in *European J. Pharmacol.*, 251, 53–59 (1994).

A number of substituted oxindoles have been disclosed as openers of BK channels by P. Hewawasam, et al., in U.S. Pat. No. 5,565,483, issued Oct. 15, 1996.

Sit, et al., in International Patent Application WO 98/23273, published Jun. 4, 1998, and corresponding U.S. Pat. No. 5,892,045, issued Apr. 6,1999, disclosed a series of 4-aryl-3-hydroxyquinolin-2-one derivatives, while Hewawasam, et al., in International Patent Application WO 99/09983, published Mar. 4, 1999, disclosed a series of 4-aryl-3-aminoquinolini-2-one derivatives which are openers of BK channels and useful in the treatment of disorders sensitive to potassium channel opening activity.

E. S. Hamanaka in U.S. Pat. No. 5,565,472, issued Oct. 15, 1996, discloses a number of 4-aryl-3-(heteroarylureido)-1,2-dihydro-2-oxo-quinoline derivatives which are inhibitors of acyl coenzyme A; cholesterol acyltransferase and are useful as hypolipidemic and antiatherosclerosis agents.

It is the object of the present invention to provide novel compounds that will modulate potassium channels, in particular, large-conductance calcium-activated potassium (BK) channels which will be useful in diseases arising from dysfunction of cellular membrane polarization and conductance.

SUMMARY OF THE INVENTION

The present invention provides novel 3-substituted-4-arylquinolin-2-one derivatives having the general formula

I

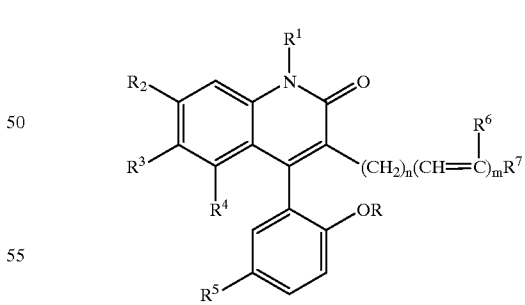

wherein R, $R^1$, $R^2$, $R^3$, $R^4$, $R^5$, $R^6$ and $R^7$ are as defined below, or a non-toxic pharmaceutically acceptable salt thereof which are openers of the large conductance calcium-activated $K^+$ channels also known as Maxi-K or BK channels. The present invention also provides pharmaceutical compositions comprising said quinolin-2-one derivatives and to the method of treatment of disorders sensitive to potassium channel opening activity such as ischemia, stroke, convulsions, epilepsy, asthma, irritable bowel syndrome, migraine, traumatic brain injury, spinal cord injury, sexual dysfunction and urinary incontinence.

DETAILED DESCRIPTION OF THE INVENTION

The present invention provides novel 3-substituted-4-arylquinolin-2-one derivatives which are potent openers of the high conductance, calcium-activated K$^+$-channels (BK channel) and which have the formula

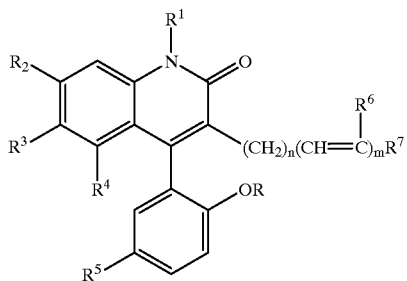

I wherein

R and R$^1$ each are independently hydrogen or methyl;

R$^2$, R$^3$ and R$^4$ each are independently hydrogen, halogen, nitro or trifluoromethyl, provided R$^2$, R$^3$, and R$^4$ are not all hydrogen;

R$^5$ is bromo, chloro or nitro;

R$^6$ is hydrogen or fluoro;

n is an integer from 0 to 6;

m is an integer of 0 or 1; and

R$^7$ is CH$_3$, —CRR$^1$OH, —CHO, —C=NOH, —COCH$_3$ or aryl optionally substituted by one or two substituents selected from the group consisting of halogen, hydroxy, methoxy, amino, acetylamino and trifluoromethyl;

or a nontoxic pharmaceutically acceptable salt thereof.

The present invention also provides a method for the treatment or alleviation of disorders associated with BK channels, such as ischemia, stroke, convulsions, epilepsy, asthma, irritable bowel syndrome, migraine, traumatic brain injury, spinal cord injury, sexual dysfunction, urinary incontinence and especially male erectile dysfunction which comprises administering together with a conventional adjuvant, carrier or diluent a therapeutically effective amount of a compound of formula I or a nontoxic pharmaceutically acceptable salt thereof.

The term "nontoxic pharmaceutically acceptable salt" as used herein and in the claims is intended to include nontoxic base addition salts with inorganic bases. Suitable inorganic bases such as alkali and alkaline earth metal bases include metallic cations such as sodium, potassium, magnesium, calcium and the like. Unless otherwise specified, the term "halogen" as used herein and in the claims is intended to include bromine, chlorine, iodine and fluorine while the term "halide" is intended to include bromide, chloride and iodide anion.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention. Certain compounds of Formula I can exist in two tautomeric forms. It should be appreciated by those skilled in the art that when R$^1$ is hydrogen on the nitrogen atom adjacent to the carbonyl carbon atom, the quinoline ring can exist in an enol form. It is intended that both enolic tautomers of the compounds of Formula I are included within the scope of the present invention.

In the method of the present invention, the term "therapeutically effective amount" means the total amount of each active component of the method that is sufficient to show a meaningful patient benefit, i.e., healing of acute conditions characterized by openers of large conductance calcium-activated K$^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

Preferred compounds for use in the method of this invention include the compounds of Formula I listed below:

4-(5-chloro-2-methoxyphenyl)-3-(hydroxymethyl)-6-(trifluoromethyl)-2(1H)-quinolinone;

4-(5-chloro-2-methoxyphenyl)-3-(hydroxymethyl)-7-(trifluoromethyl)-2(1H)-quinolinone;

4-(5-chloro-2-methoxyphenyl)-1,2-dihydro-2-oxo-6-(trifluoromethyl)-3-quinolinecarboxaldehyde;

4-(5-chloro-2-methoxyphenyl)-3-(3-hydroxy-1-propenyl)-6-(trifluoromethyl)-2(1H)-quinolinone;

4-(5-chloro-2-methoxyphenyl)-3-(3-hydroxypropyl)-6-(trifluoromethyl)-2(1H)-quinolinone;

4-(5-chloro-2-hydroxyphenyl)-3-(hydroxymethyl)-6-(trifluoromethyl)-2(1H)-quinolinone;

4-(5-chloro-2-hydroxyphenyl)-3-(3-hydroxy-1-propenyl)-6-(trifluoromethyl)-2(1H)-quinolinone;

4-(5-cholro-2-hydroxyphenyl)-3-(3-hydroxypropyl)-6-(trifluoromethyl)-2(1H)-quinolinone;

(E)-4-(5-chloro-2-hydroxyphenyl)-3-(2-f luoro-3-hydroxy-1-propenyl)-6-trifluoromethyl)-2(1H)-quinolinone;

(Z)-4-(5-chloro-2-hydroxyphenyl)-3-(2-fluoro-3-hydroxy-1-propenyl)-6-trifluoromethyl)-2(1H)-quinolinone;

(E)-4-(5-chloro-2-methoxyphenyl)-3-(2-fluoro-3-hydroxy-1-propenyl)-6-(trifluoromethyl)-2(1H)-quinolinone;

(Z)-4-(5-chloro-2-methoxyphenyl)-3-(2-fluoro-3-hydroxy-1-propenyl)-6-(trifluoromethyl)-2(1H)-quinolinone;

4-(5-chloro-2-hydroxyphenyl)-3-(2-hydroxyethyl)-6-(trifluoromethyl)-2(1H)-quinolinone;

4-(5-chloro-2-methoxyphenyl)-3-(2-hydroxyethyl)-6-trifluoromethyl-2(1H)-quinolinone;

4-(5-chloro-2-methoxyphenyl)-3-(4-methoxyphenyl)-6-(trifluoromethyl)-2(1H)-quinolinone;

4-(5-chloro-2-methoxyphenyl)-3-[(4-methoxyphenyl)methyl]-6-(trifluoromethyl)-2(1H)-quinolinone;

4-(5-chloro-2-methoxyphenyl)-3-(4-nitrophenyl)-6-(trifluoromethyl)-2(1H)-quinolinone;

4-(5-chloro-2-methoxyphenyl)-3-(4-aminophenyl)-6-(trifluoromethyl)-2(1H)-quinolinone;

4-(5-chloro-2-hydroxyphenyl)-3-(3,4-dimethoxyphenyl)-6-(trifluoromethyl)-2(1H)-quinolinone;

4-(5-chloro-2-hydroxyphenyl)-3-(2,4-dihydroxyphenyl)-6-(trifluoromethyl)-2(1H)-quinolinone;

4-(5-chloro-2-hydroxyphenyl)-3-(4-hydroxyphenyl)-6-(trifluoromethyl)-2(1H)-quinolinone;
4-(5-chloro-2-hydroxyphenyl)-3-[(4-hydroxyphenyl)methyl]-6-(trifluoromethyl)-2(1H)-quinolinone;
4-(5-chloro-2-hydroxyphenyl)-3-(4-acetamidophenyl)-6-(trifluoromethyl)-2(1H)-quinolinone;
4-(5-chloro-2-hydroxyphenyl)-3-(4-aminophenyl)-6-(trifluoromethyl)-2(1H)-quinolinone;
4-(5-chloro-2-hydroxyphenyl)-3-[2-(4-hydroxyphenyl)ethyl]-6-(trifluoromethyl)-2(1H)-quinolinone;
4-(5-chloro-2-hydroxyphenyl)-3-methyl-6-(trifluoromethyl)-2(1H)-quinolinone;
4-[4-(5-chloro-2-hydroxyphenyl)-1,2-dihydro-2-oxo-6-(trifluoromethyl)quinolin-3-yl]-3-buten-2-one;
4-(5-chloro-2-hydroxyphenyl)-1,2-dihydro-2-oxo-6-(trifluoromethyl)-3-quinolinecarboxaldehyde oxime;
4-(5-chloro-2-methoxyphenyl)-1,2-dihydro-2-oxo-6-(trifluoromethyl)-3-quinolinecarboxaldehyde oxime; and
4-(5-chloro-2-hydroxyphenyl)-3-(2-hydroxy-2-methylpropyl)-6-(trifluoromethyl)-2(1H)-quinolinone.

The compounds of Formula I may be prepared by various procedures such as those illustrated herein in the examples and in the Reaction Schemes described in the specific embodiments and variations thereof which would be evident to those skilled in the art.

The following Reaction Schemes 1–11 illustrate representative general procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

REACTION SCHEME 1

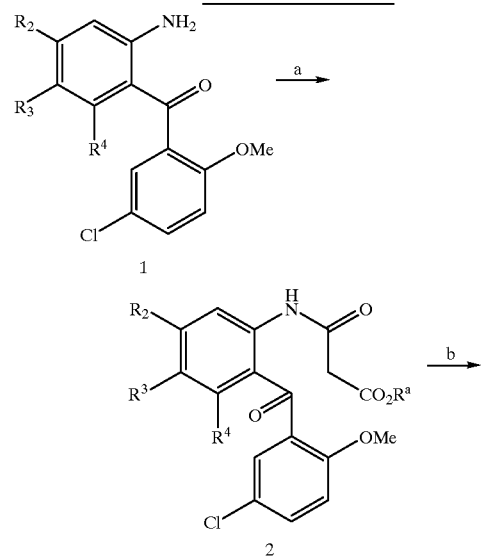

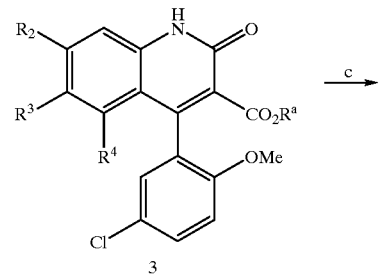

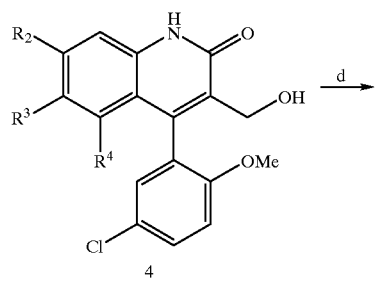

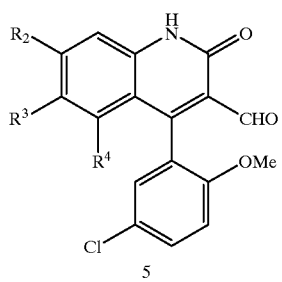

(a) ClC(O)CH$_2$CO$_2$R$^a$, pyridine, CH$_2$Cl$_2$ 0° C. to RT
(b) KO$^t$Bu, THF, reflux
(c) Dibal-H, THF-hexanes, -78° C. to RT
(d) MnO$_2$, CH$_2$Cl$_2$ The preparation of 2(1H)-quinolinones of Formulae 4 and 5 is illustrated in Reaction Scheme 1. Acylation of the compound of Formula 1 with an acid chloride as shown in the Reaction Scheme provided the amide of Formula 2 wherein R$^a$ is hydrogen or C$_{1-4}$ alkyl which may be cyclized and dehydrated to the quinolinone of Formula 3 by treatment with a base such as potassium tert-butoxide in an inert organic solvent. Exposure of the ester of Formula 3 to a reducing agent such as diisobutyl aluminum hydride affords the primary alcohol of Formula 4 which can then be advantageously oxidized with an oxidant such as manganese dioxide to yield the desired aldehyde of Formula 5.

REACTION SCHEME 2

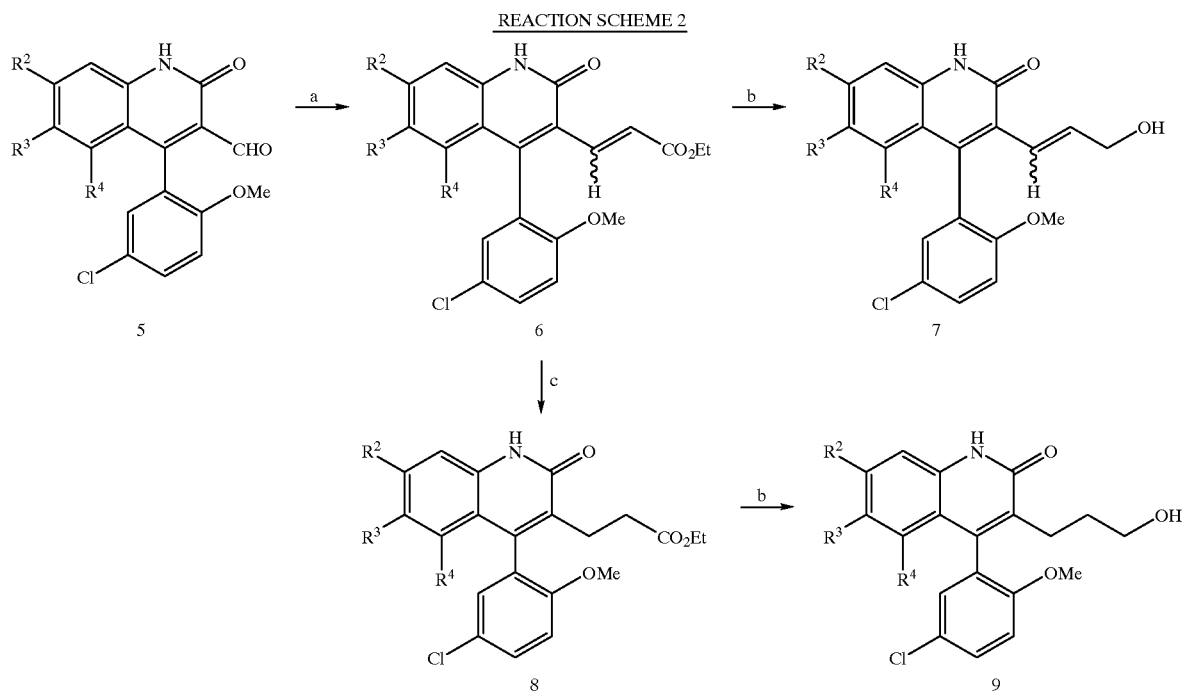

(a) EtOC(O)CH₂P(O)(OEt)₂, NaH, DMF
(b) Dibal-H, THF, -78° C.
(c) PtO₂, EtOH-HCl, H₂ (60 psi)

As illustrated in Reaction Scheme 2, the homologation of the aldehyde of Formula 5 can readily be accomplished with a phosphonate reagent to produce the unsaturated ester of Formula 6 as a mixture of (E)- and (Z)-isomers which then be separated using column chromatography. Reduction of the ester of Formula 6 may be carried out with a reducing agent such as diisobutyl aluminum hydride to afford the corresponding allylic alcohol of Formula 7. Alternatively, when it is desired to prepare the compound of Formula 9, the ester of Formula 6 is selectively reduced under hydrogenation conditions to reduce the double bond and provide the saturated ester of Formula 8. Treatment of the ester of Formula 8, under conditions similar to the reduction of the ester of Formula 6 will afford the corresponding alcohol of Formula 9.

REACTION SCHEME 3

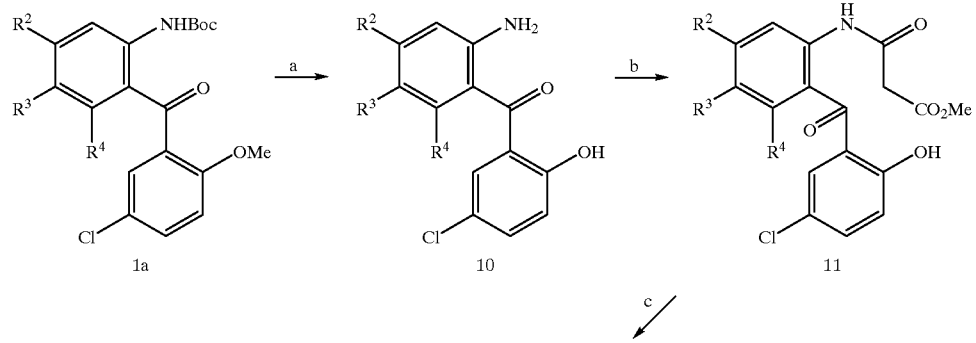

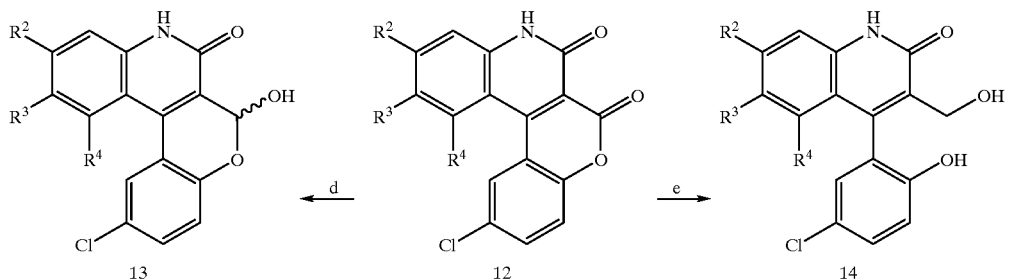

(a) BBr₃, CH₂Cl₂, -78 to 0° C.
(b) ClC(O)CH₂CO₂Me, pyridine, CH₂Cl₂
(c) KO$^t$Bu, THF, reflux
(d) Dibal-H, THF, -78° C.
(e) Dibal-H, CH₂Cl₂, -78° C.

In Reaction Scheme 3, the butyloxycarbonyl (BOC) and methyl groups can be removed simultaneously by treatment of the compound of Formula 1a with boron tribromide (BBr₃) to give the aniline of Formula 10. Acylation of the aniline of Formula 10 afforded the corresponding amide of Formula 11, which is readily cyclized and dehydrated under basic conditions with potassium tert-butoxide to provide the lactone of Formula 12. Partial reduction of the lactone with diisobutyl aluminum hydride in THF produced the intermediate lactol of Formula 13. Alternatively, it has been found that by changing solvents from THF to methylene chloride, the lactone of Formula 12 can be reduced with diisobutyl aluminum hydride to provide the desired alcohol of Formula 14.

REACTION SCHEME 4

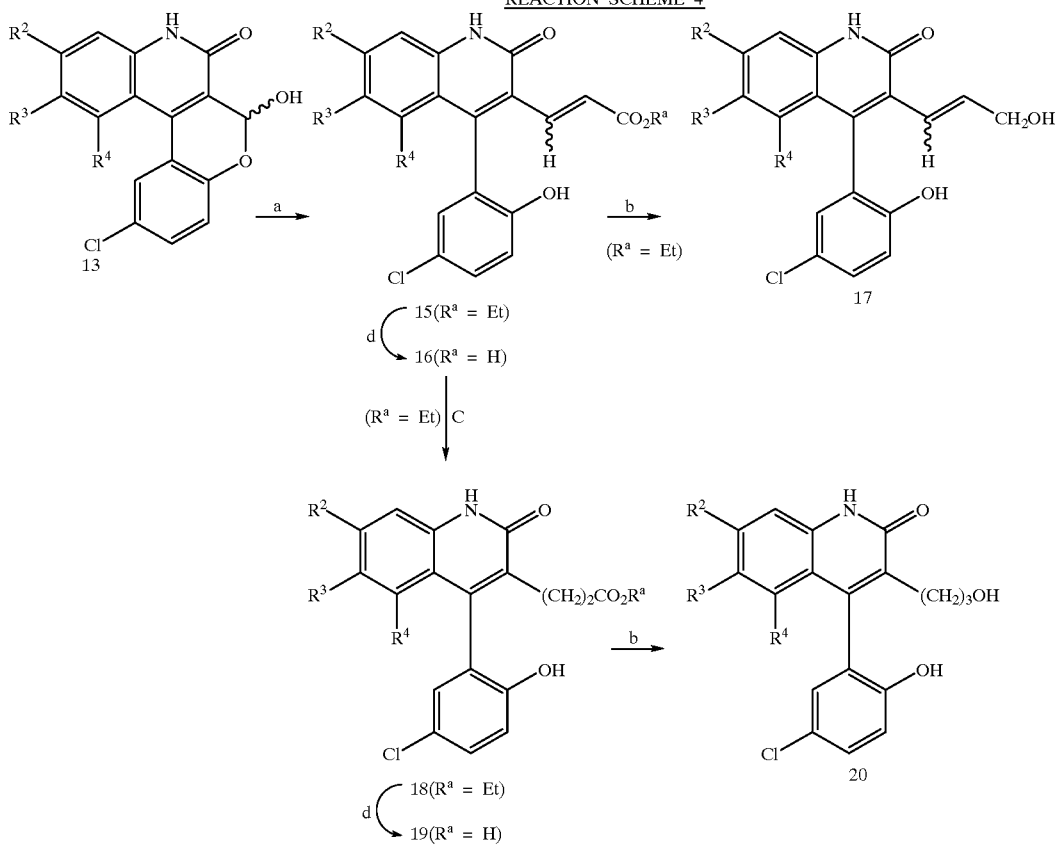

(a) EtOC(O)CH₂P(O)(OR$^a$)₂, NaH, DMF
(b) Dibal-H, THF-hexanes, -78° C. to RT
(c) PtO₂, EtOH—HCl, H₂ (60 psi)
(d) NaOH, EtOH, RT When it is desired to prepare the compound of Formulae 17 and 20, the intermediate lactol of Formula 13 may be treated as shown in Reaction Scheme 4 with a phosphonate reagent to afford the unsaturated ester of Formula 15 and then, if desired, be saponified to produce the unsaturated acid of Formula 16. Reduction of the ester of Formula 15 with aluminum hydride affords the corresponding unsaturated alcohol of Formula 17. Alternatively, the hydrogenation of the double bond of the compound of Formula 15 yields the ester of Formula 18, which may be either saponified to produce the acid of Formula 19, or reduced with aluminum hydride to yield the desired alcohol of Formula 20.

Reaction Scheme 5 illustrates the homologation of the intermediate lactol of Formula 13 with a fluorophosphonate, as described in step (a) in the Reaction Scheme, to afford the unsaturated α-fluoroester ester of Formula 21 as a mixture of (E)- and (Z)-isomers. The crude mixture of esters of Formula 21 may be reduced with aluminum hydride, and the resulting mixture of alcohols are advantageously separated by column chromatography to afford the (E)-olefin of Formula 23 and the (Z)-olefin of Formula 25. In a similar manner, the aldehyde of Formula 5 which contains a methyl ether can be converted to the corresponding desired olefins of Formulae 24 and 26.

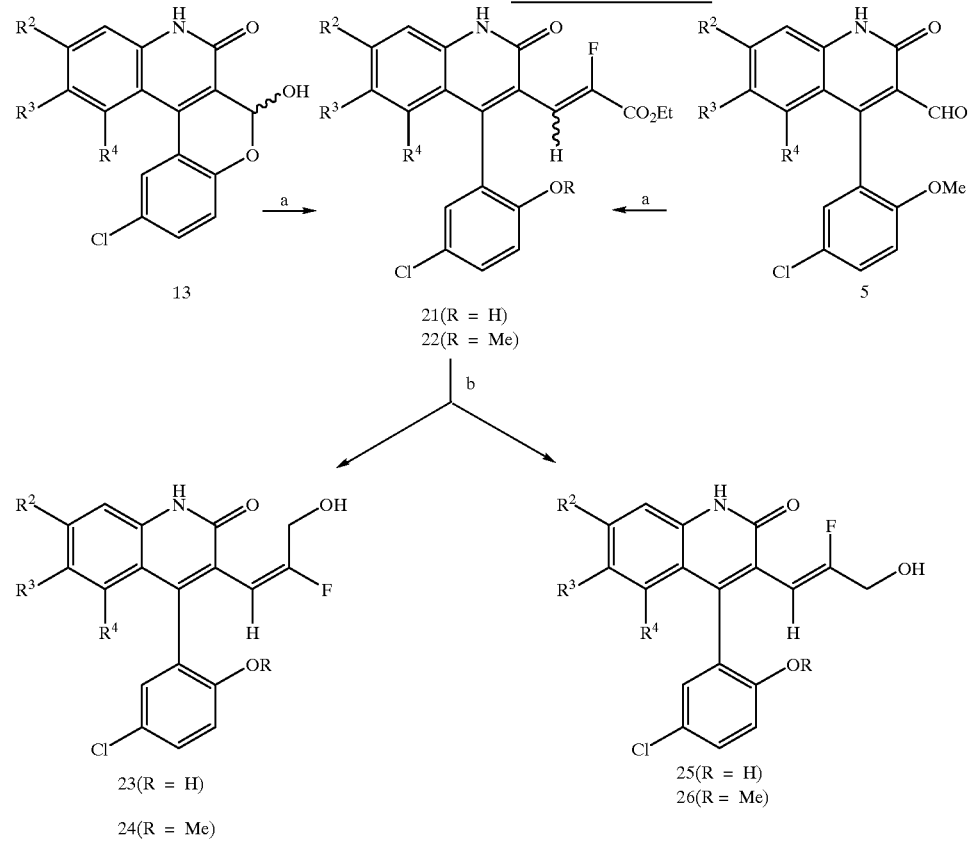

REACTION SCHEME 5

(a) EtOC(O)CHFP(O)(OEt)$_2$, NaH, DMF
(b) Dibal-H, CH$_2$Cl$_2$, -78° C. to RT

REACTION SCHEME 6

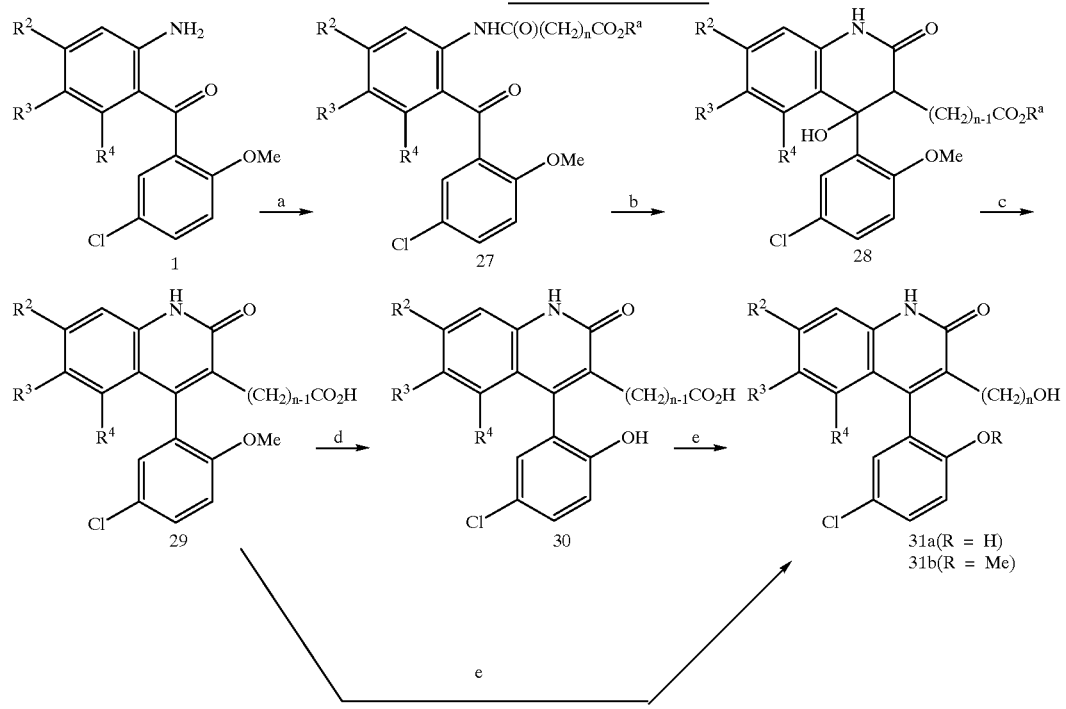

(a) ClC(O)(CH₂)ₙCO₂Rᵃ, pyridine, CH₂Cl₂
(b) KHMDS, THF, -78° C.
(c) 35% HBr—AcOH, toluen, 80-90° C.
(d) pyridine, HCl, 180-200° C.
(e) BH₃·SMe₂, THF, -10° C. to RT The preparation of compounds of Formulae 31a and 31b is illustrated in Reaction Scheme 6. Acylation of the aniline of Formula 1 with an acid chloride provides the corresponding amide. The amide of Formula 27 may be cyclized under basic conditions to give the dehydrohydroxyquinolinone of Formula 28, which may then be dehydrated and deesterified under acidic conditions such as HBr/AcOH or pTsOH, to afford the quinolinone of Formula 29. If desired, removal of the methyl ether can be accomplished with pyridine hydrochloride at elevated temperatures to give the corresponding phenol of Formula 30. Reduction of the acid of Formula 30 then provides the alcohol of Formula 31a as the phenol. Alternatively, if the methyl ether of the phenol is desired, direct reduction of the carboxylic acid of Formula 29 with borane provides the corresponding alcohol of Formula 31b.

REACTION SCHEME 7

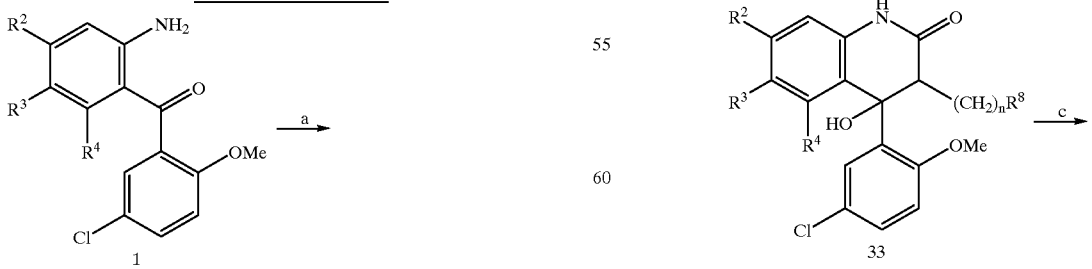

-continued

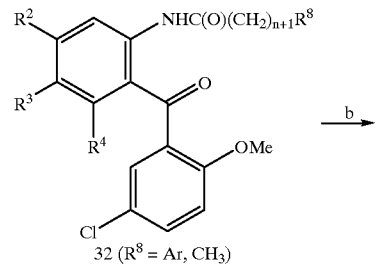

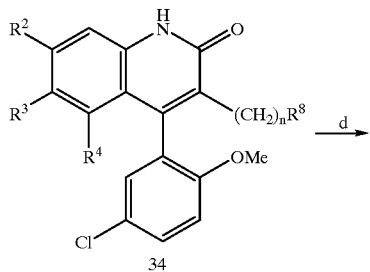

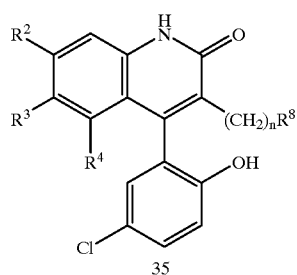

(a) ClC(O)(CH$_2$)$_{n+1}$R$^8$, pyridine, CH$_2$Cl$_2$
(b) KHMDS, THF, -78° C.
(c) H$^+$
(d) pyridine.HCl, 180–200° C.

The compound of Formulae 34 and 35 wherein n is 0 to 6 and R$^8$ is C$_{1-4}$ alkyl or aryl optionally substituted by one or two substituents selected from the group consisting of halogen, hydroxy, methoxy, amino, acetylamino and trifluoromethyl, may be prepared by a similar approach to that outlined in Reaction Scheme 6. Thus, Reaction Scheme 7 illustrates the acylation of the compound of Formula 1, followed by cyclization and dehydration to give the 3-substituted quinoline of Formula 34 as the methyl ether. Demethylation of the compound of Formula 34 with pyridine hydrochloride at elevated temperatures provides the corresponding phenol compound of Formula 35.

REACTION SCHEME 8

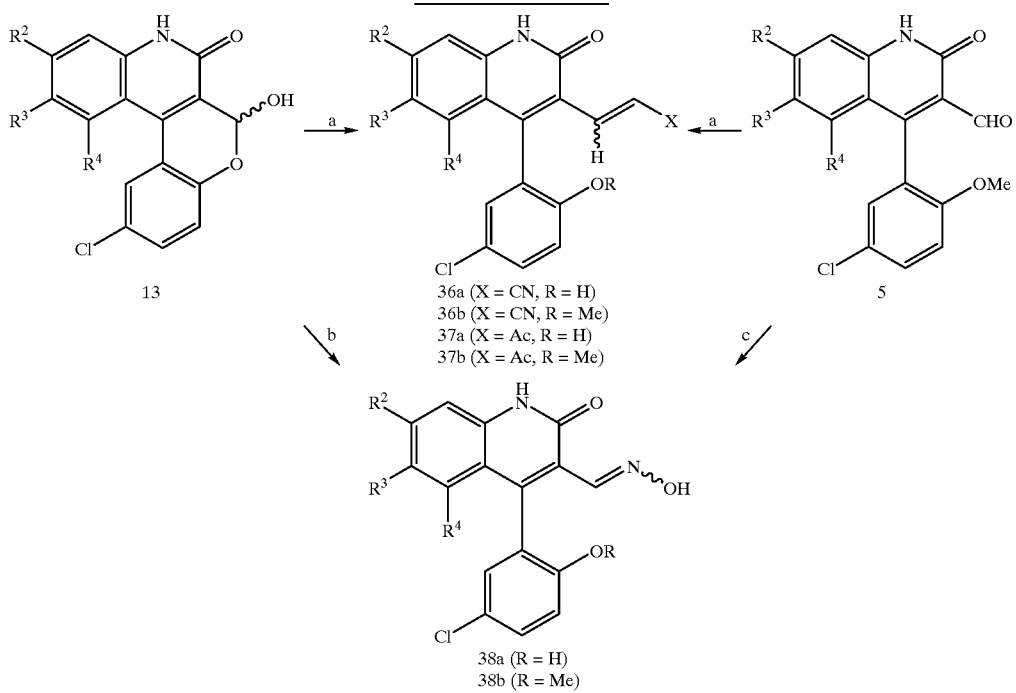

(a) (MeO)$_2$P(O)CH$_2$X, NaH, DMF
(b) NH$_2$OH.HCl, Et$_3$N, THF
(c) NH$_2$OH.HCl, an. NaOAc, EtOH

As shown in Reaction Scheme 8, homologation of the intermediate lactol of Formula 13 with a cyano phosphonate or phosphonoacetate reagent provides the corresponding unsaturated nitrile of Formula 36a or acetate of Formula 37a, respectively. Similarly, the methyl ether analogs of Formulae 36b and 37b can be synthesized starting with the aldehyde of Formula 5 and treatment with either a cyano phosophonate or phosphonoacetate reagent, respectively. The oxime of Formula 38a can be prepared from the intermediate lactol of Formula 13 by treating the lactol with hydroxyl amine. Similarly, the methyl ether of Formula 38b, can be prepared from the aldehyde of Formula 5.

treated with a catalytic amount of acid in refluxing toluene. Upon attempted purification of lactone of Formula 39 on silica gel and employing methanol as one of the eluting solvents, the lactone may be converted to the ester of Formula 30b. When it is desired to prepare the substituted alcohol of Formula 40, the lactone of Formula 39 is treated with an excess of a lithium reagent such as methyl lithium to produce the disubstituted alcohol of Formula 40 or

REACTION SCHEME 9

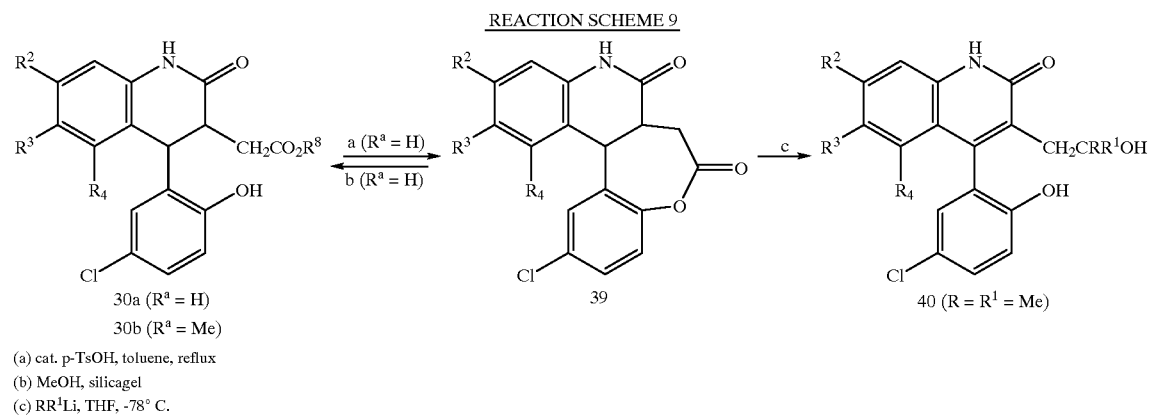

(a) cat. p-TsOH, toluene, reflux
(b) MeOH, silicagel
(c) RR$^1$Li, THF, -78° C.

Reaction Scheme 9 illustrates the formation of the lactone of Formula 39 when the hydroxy acid of Formula 30a is treated with a catalytic amount of acid in refluxing toluene.

alternately, with an equivalent amount to produce a mono-substituted alcohol.

REACTION SHCEME 10

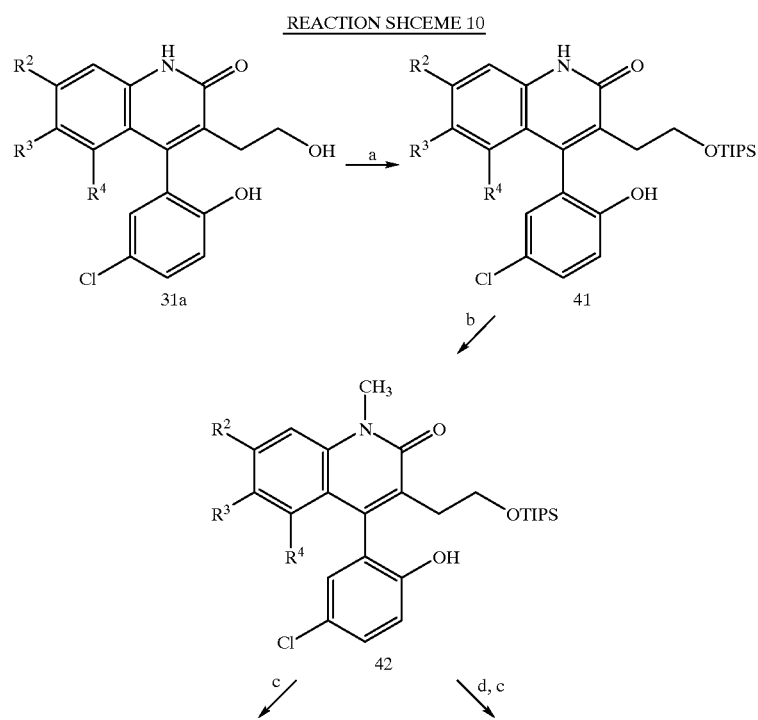

-continued

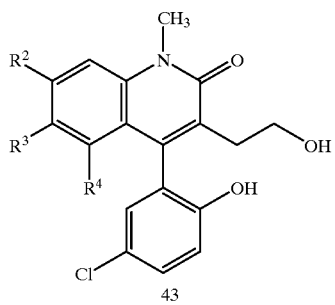

43

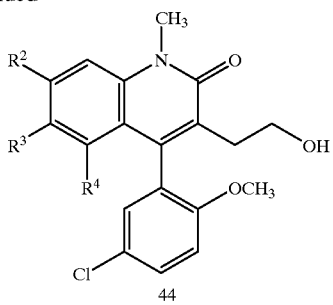

44

(a) TIPSCl, Imidazole, DMF
(b) nBuLi, CH₃I, THF
(c) TBAF, THF
(d) K₂CO₃, (CH₃O)₂SO₂, Acetone The preparation of the N-methyl compounds of Formulae 43 and 44 are depicted in Reaction Scheme 10. Silylation of the alcohol of Formula 31a with triisopropylsilyl (TIPS) chloride provided the silyl protected ether of Formula 41. N-alkylation with an alkyl halide such as methyl iodide afforded the compound of Formula 42, which may be desilylated with a fluoride reagent, step (c), to give the alcohol of Formula 43. When it is desired to prepare the methylated phenol, the compound of Formula 41 is treated with dimethylsulfate followed by desilylation to afford the dimethyl analog of Formula 44.

REACTION SHCEME 11

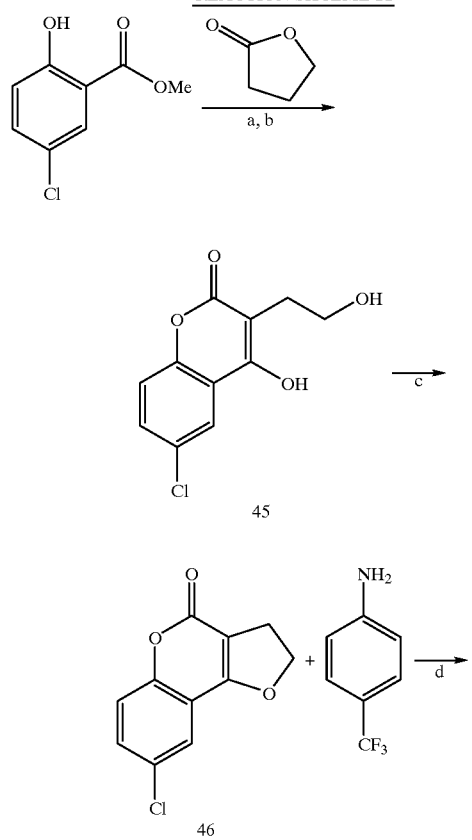

-continued

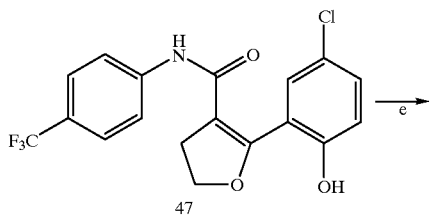

47

[structure 31a]

31a (a) LiHMDS/THF, -78° C. TO RT
(b) 12N HCl
(c) pTSA, Toluene, reflux
(d) LiHMDS
(e) hv, MeOH The preparation of the compound of Formula 31a is advantageously prepared by the reactions illustrated in Reaction Scheme 11. The coumarin compound of Formula 45 is advantageously prepared by condensing γ-butyrolactone with the methyl ester of chlorosalicylic acid which is then readily cyclized with acid to produce the benzopyran-4-one of Formula 46. Treatment of compound 46 with p-trifluoromethylaniline as illustrated in step (d) produced the dihydrofuran of Formula 47 which is then subjected to photocyclization in an inert organic solvent to afford the compound of Formula 31a.

In a preferred embodiment of the invention the compounds of Formula I have the formula

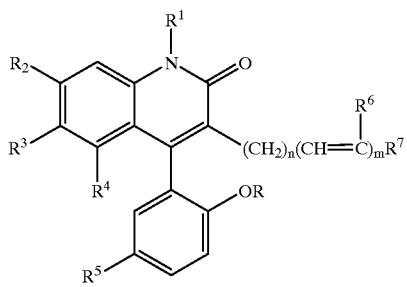

wherein R and $R^1$ each are independently hydrogen or methyl; $R^2$, $R^3$ and $R^4$ each are independently hydrogen, halogen, nitro or trifluoromethyl, provided $R^2$, $R^3$, and $R^4$ are not all hydrogen; $R^5$ is bromo, chloro or nitro; $R^6$ is hydrogen or fluoro; n is an integer from 0 to 6; m is an integer of 0 or 1; and $R^7$ is —$CH_3$, —$CRR^1OH$, —CHO, —C═NOH, —$COCH_3$ or aryl optionally substituted by one or two substituents selected from the group consisting of halogen, hydroxy, methoxy, amino, acetylamino and trifluoromethyl; or a nontoxic pharmaceutically acceptable salt thereof.

In another preferred embodiment of the invention, the compounds of the invention include those wherein R and $R^1$ each are independently hydrogen or methyl; $R^2$, $R^3$ and $R^4$ each are independently hydrogen, chloro, nitro or trifluoromethyl, provided $R^2$, $R^3$ and $R^4$ are not all hydrogen; $R^5$ is chloro; $R^6$ is hydrogen or fluoro; n is 0, 1, or 2; m is 0 or 1; and $R^7$ is —$CH_3$, —$CH_2OH$, —CHO, —C═NOH, —$COCH_3$ or aryl optionally substituted by halogen, hydroxy, methoxy, amino, acetylamino or trifluoromethyl; or a nontoxic pharmaceutically acceptable salt thereof.

In yet another more preferred embodiment of the invention the compound of Formula I include those wherein R is hydrogen or methyl; $R^1$ and $R^4$ are hydrogen; $R^2$ and $R^3$ each are independently trifluoromethyl; $R^5$ is chloro; $R^6$ is hydrogen; n is 0, 1, or 2; m is 0 or 1; and $R^7$ is —$CH_2OH$ or aryl optionally substituted by halogen, hydroxy, methoxy, amino, acetylamino or trifluoromethyl; or a nontoxic or a nontoxic pharmaceutically acceptable salt thereof.

In another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, stroke, convulsions, asthma, irritable bowel syndrome, migraine, traumatic brain injury, urinary incontinence, and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity.

In still another aspect, this invention provides pharmaceutical compositions comprising at least one compound of Formula I in combination with a pharmaceutical adjuvant, carrier or diluent.

BIOLOGICAL ACTIVITY

Potassium ($K^+$) channels are structurally and functionally diverse families of $K^+$-selective channel proteins which are ubiquitous in cells, indicating their central importance in regulating a number of key cell functions [Rudy, B., Neuroscience, 25: 729–749 (1988)]. While widely distributed as a class, $K^+$ channels are differentially distributed as individual members of this class or as families. [Gehlert, D. R., et al., Neuroscience, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the large-conductance $Ca^{2+}$-activated $K^+$ channels (Maxi-K or BK channels), is regulated by transmembrane voltage, intracellular $Ca^{2+}$, and a variety of other factors such as the phosphorylation state of the channel protein. [Latorre, R., et al., Ann. Rev. Pysiol., 51: 385–399 (1989)]. The large, single channel-conductance (generally>150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., J. Pharmacol. Exp. Ther., 267: 1277–1285 (1993)].

Openers of BK channels exert their cellular effects by increasing the open probability of these channels [McKay, M. C., et al., J. Neurophysiol., 71: 1873–1882 (1994); and Olesen, S.-P., Exp. Opin. Invest. Drugs, 3: 1181–1188 (1994)]. This increase in the opening of individual BK channels collectively results in the hyperpolarization of cell membranes, particularly in depolarized cells, produced by significant increases in whole-cell BK-mediated conductance.

The ability of compounds described in the present invention to open BK channels and increase whole-cell outward ($K^+$) BK-mediated currents was assessed under voltage-clamp conditions by determining their ability to increase cloned mammalian (mSlo or hSlo) BK —mediated outward current heterologously expressed in Xenopus oocytes [Butler, A., et al., Science, 261: 221–224 (1993); and Dworetzky, S. I., et al., Mol. Brain Res., 27: 189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., J. Biol. Chem., 265: 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compounds profiled did not effect non-BK native currents in the oocytes. All compounds were tested in at least 5 oocytes and are reported at the single concentration of 20 μM; the effect of the selected compounds of Formula I on BK current was expressed as the percent of control IBTX-sensitive current and is listed in Table I. Recordings were accomplished using standard two-electrode voltage clamp techniques [Stuhmer, W., et al., *Methods in Enzymology*, Vol. 207: 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), NaHCO$_3$ (2.4), KCl (1.0), HEPES (10), MgSO$_4$ (0.82), Ca(NO$_3$)$_2$ (0.33), CaCl$_2$ (0.41); pH 7.5.

TABLE 1

| Ex. No. | BK Current* |
|---|---|
| 3 | + |
| 4 | + |
| 8 | ++ |
| 9 | ++ |
| 17 | + |
| 18 | + |
| 20 | ++ |
| 21 | ++ |
| 30 | ++ |
| 32 | ++ |
| 34 | ++ |
| 39 | ++ |

* at 20 μM expressed as percent increase over BK current in controls
+ = 100–200%
++ = >200%

To determine the ability of these compounds to reduce cell loss resulting from neuronal ischemia, a standard rodent model of permanent focal ischemia, involving occlusion of the middle cerebral artery in the spontaneously hypertensive rat (middle cerebral artery occlusion (MCAO) model) was employed [Tamura, A., et al., *Journal of Cerebral Blood Flow and Metabolism*, Volume 1, 53–60, (1981)].

Selected compounds have been evaluated in the focal stroke model involving permanent MCAO in the spontaneously hypertensive rat. This procedure results in a reliably large neocortical infarct volume that is measured by means of vital dye exclusion in serial slices through the brain 24 hours after MCAO. In the present test, compounds were administered using an intravenous route of administration at 2 hours after occlusion. For example, in this model, the compound of Example 21 reduced the cortical infarct volume by about 25% when administered (0.003 mg/kg) as a single bolus 2 hours after middle cerebral artery occlusion as compared to vehicle-treated (2% DMSO, 98% propylene glycol) control.

The in vivo model on erectile function is described fully in the scientific literature [Rehman, J., Chenven, E., Brink, P. Peterson, B., Wolcott, B., Wen, Y. P., Melman, A., Christ, G.: Diminished neurogenic but not pharmacological erections in the 2- to 3-month experimentally diabetic F-344 rat. *Am. J. Physiol.* 272: H1960-H1971, (1997)]. Briefly, rats (250–600 g) were anesthetized using sodium pentobarbital, the abdomen opened and the cavernous nerve identified. A pressure catheter was placed in the right corpus cavernosum (crus) to measure intracavernous pressure (ICP). A second catheter was introduced into the carotid artery to measure blood pressure. Test compound (0.1, 0.3 and 1 mg/kg iV.) or vehicle (PEG 400) was given via a catheter placed into the jugular vein.

Control intracavernous pressure responses were elicited by electrically stimulating the cavernous nerve via bipolar stimulating electrodes (20 Hz, 0.22 ms pulse width). Stimulus amplitude (0.2–20 mA) was adjusted to produce a submaximal intracavernous pressure response (typically 0.2 or 0.5 mA). A series of control intracavernous pressure responses were then obtained using a constant stimulus amplitude. Test compound or vehicle was then administered (200 μl i.v bolus) and the cavernous nerve was restimulated to evoke a cavernous pressure response at various times post-drug administration. Animals were excluded from the study if the initial ICP responses to nerve stimulation were unstable ("spiky" responses) or if there were time-dependent variations in the magnitude of the control responses. Animals were also excluded if the control ICP/BP response fell outside the 0.3–0.6 range. A repeated measures ANOVA was used for the evaluation of statistical significance.

The compound of Example 20 (0.1–1 mg/kg) produced an augmentation of the ICP/BP responses elicited by submaximal stimulation of the cavernous nerve. A significant increase in the ICP/BP ratio was observed at doses from 0.1–1.0 mg/kg of compound tested.

The results of the above biological tests demonstrates that the compounds of the instant invention are potent openers of the large-conductance calcium-activated K$^+$ channels (Maxi-K or BK channels). Thus, the compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, sexual dysfunction, urinary incontinence and especially male erectile dysfunction, other disorders sensitive to BK channel activating activity.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 $\mu$g/kg to 10 mg/kg body weight and preferrably, from about 0.1 $\mu$g/kg to 5 mg/kg body weight for oral administration. For parenteral administration, the dose may be in the range of 0.1 $\mu$g/kg to 1 mg/kg body weight for intravenous administration The active ingredient will preferably be administered in equal doses from one to four times a day. However, usually a small dosage is administered, and the dosage is gradually increased until the optimal dosage for the host under treatment is determined.

The compounds of the present invention may be employed alone or in combination with other suitable therapeutic agents useful in the treatment of sexual dysfunction such as cGMP PDE inhibitors and particularly cGMP PDE V inhibitors such as sildenafil. Exemplary of the therapeutic agents are PDE V inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), anthranilic acid derivatives (see WO 95/18097), fused heterocycles (see WO 98/07430) and thienopyrimidines (see DE 19632423).

The above therapeutic agents, when employed in combination with the compounds of the present invention, may be used, for example, in those amounts indicated in the Physician's Desk Reference (PDR) or as otherwise determined by one of ordinary skill in the art.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the scope of the invention.

DESCRIPTION OF SPECIFIC EMBODIMENTS

In the following examples, all temperatures are given in degrees Centigrade. Melting points were recorded on a Gallenkamp capillary melting point apparatus are uncorrected. Proton magnetic resonance ($^1$H NMR) spectra were recorded on a Bruker AC 300 spectrometer. All spectra were determined in the solvents indicated and chemical shifts are reported in $\delta$ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular weight (MH$^+$) or (M–H)$^-$ was determined on a Finnigan TSQ 7000. The element analyses are reported as percent by weight. Unless otherwise indicated in the Specific Embodiments, R$^2$ and R$^4$ are H in the descriptive title of the Examples.

EXAMPLE 1

4-(5-Chloro-2-methoxyphenyl)-1,2-dihydro-2-oxo-6-(trifluoromethyl)-3-quinolinecarboxylic acid, methyl ester (3, R$^3$=CF$_3$, R$^a$=CH$_3$)

Step A: N-[2-[(5-Chloro-2-methoxyphenyl) carbonyl]-4-(trifluoromethyl) phenyl]aminocarboxylic acid, 1,1-dimethylethyl ester A stirred neat mixture of 4-aminobenzotrifluoride (35 g, 0.218 mol) and (Boc)$_2$O (52.4 g, 0.24 mol) was heated at 80° C. for 2 to 3 hours until CO$_2$ evolution ceased. The mixture was allowed to cool and the $^t$BuOH was rotary evaporated. The resultant white solid was recrystallized from hexanes/ether to provide white needles (50.6 g, 89%) of N-(tert-butoxycarbonyl)-4-aminobenzotrifluoride.

Tert-BuLi (130 mL, 0.22 mol, 1.7M in cyclohexane) was added over 20 minutes to a cold (–78° C.) stirred solution of N-Boc-4-aminobenzotrifluoride (26.2 g, 0.1 mol) in dry THF (130 mL) under argon. The resultant yellow partial solution was warmed to –45° to –40° C. and maintained for 2 hours. The resultant thick yellow slurry of the dianion was cooled to –78° C. and neat dry methyl 5-chloro-2-methoxybenzoate (22.1 g, 0.11 mol) was added rapidly. The resultant yellow-brown solution was warmed to –40° C. and maintained for 1 hour. The reaction was diluted with ether (200 mL) and quenched with 1N HCl (250 mL) and then allowed to warm to room temperature. The organic layer was separated, washed with water, brine and then dried (Na$_2$SO$_4$). Evaporation of solvents gave a light-yellow solid (49.9 g) which was triturated with ether to afford 31.9 g of the desired titled compound: mp 148–150° C.; IR (KBr, cm$^{-1}$) 3280, 1725, 1640, 1530, 1320, 1250, 1150;

$^1$H NMR (300 MHz, DMSO-d$_6$): $\delta$ 1.41 (9 H, s), 3.58 (3 H, s), 7.19 (1 H, d, J=8.9 Hz), 7.49 (1 H, d, J=2.7 Hz), 7.58 (1 H, d, J=2.6 Hz), 7.60 (1 H, dd, J=8.9 and 2.7 Hz), 7.93 (1 H, dd, J=8.7 and 1.9 Hz), 8.12 (1 H, s), 8.15 (1 H, m), 10.35 (1 H, s); MS m/e 430 (MH$^+$). Anal. Calcd. for C$_{20}$H$_{19}$ClF$_3$NO$_4$: C, 55.88; H, 4.45; N, 3.25. Found: C, 55.51; H, 4.38; N, 3.26.

Step B: 1-[2-Amino-5-(trifluoromethyl)phenyl]-1'-(5-chloro-2-methoxyphenyl) methanone (1, R$^3$=CF$_3$)

To a stirred solution of N-[2-[(5-chloro-2-methoxyphenyl) carbonyl]-4-(trifluoromethyl)phenyl] aminocarboxylic acid, 1,1-dimethylethyl ester (19 g, 0.044 mol) in ethanol (300 mL), 3N HCl was added. The resultant suspension was heated to reflux for 3 hours. The progress of the hydrolysis was monitored by TLC. The reaction mixture was cooled and poured into cold water (500 mL). The product was extracted with ether (2×200 mL) and the combined ether extracts were washed with water, brine and then dried (Na$_2$SO$_4$). Evaporation of the ether gave a golden yellow viscous oil which upon standing overnight solidified to afford a beige solid (14.6 g, 100%): mp 90–92° C.; IR (KBr, cm$^{-1}$) 3340, 3470, 1640, 1320, 1240, 1150, 1025;

$^1$H NMR (300 MHz, DMSO-d$_6$): δ 3.68 (3 H, s), 6.97 (1 H, d, J=8.8 Hz), 7.19 (1 H, d, J=8.9 Hz), 7.26 (1 H, d, J=1.1 Hz), 7.36 (1 H, d, J=2.7 Hz), 7.53 (2 H, m), 7.92 (2 H, brd s); MS m/e 330 (MH$^+$). Anal. Calcd. for C$_{15}$H$_{11}$ClF$_3$NO$_2$: C, 54.64; H, 3.36; N, 4.25. Found: C, 54.65; H, 3.37; N, 4.16.

Step C: 3-[[2-[(5-Chloro-2-methoxyphenyl)carbonyl]-4-(trifluoromethyl)phenyl]amino]-3-oxopropanoic acid, methyl ester (2, R$^3$=CF$_3$, R$^a$=CH$_3$)

A solution of methyl malonyl chloride (1.3 mL, 12 mmol) in anhydrous CH$_2$Cl$_2$ (10 mL) was added dropwise to a stirred cold (0° C.) solution of 1-[2-amino-5-(trifluoromethyl)phenyl]-1'-(5-chloro-2-methoxyphenyl) methanone prepared in Step B (3.3 g, 10 mmol) and anhydrous pyridine (0.97 mL, 12 mmol) in anhydrous CH$_2$Cl$_2$ (30 mL) under nitrogen. The resultant mixture allowed to warm to room temperature and maintained for 1 hour. The reaction was cooled to 0° C. and then quenched with 1N HCl (1 mL). The organic layer was separated and consecutively washed with saturated NaHCO$_3$, water, brine and then dried (MgSO$_4$). Evaporation of CH$_2$Cl$_2$ gave a beige solid (4.28 g) which was triturated with ether to afford the title compound as a light-yellow solid (3.98 g, 93%): mp 138–140° C.; IR (KBr, cm$^{-1}$) 1120, 1314,1530,1644, 1712, 1738;

$^1$H NMR (300 MHz, CDCl$_3$): δ 3.57 (2 H, s), 3.66 (3 H, s), 3.81 (3 H, s), 6.92 (1 H, d, J=8.8 Hz), 7.38 (1 H, d, J=2.6 Hz), 7.47 (1 H, dd, J=8.8 and 2.6 Hz), 7.65 (1 H, s), 7.75 (1 H, d, J=8.9 Hz), 8.84 (1 H, d, J=8.8 Hz), 11.91 (1 H, brd s); MS m/e 428 (M-H)$^-$.

Step D: 4-(5-Chloro-2-methoxyphenyl)-1,2-dihydro-2-oxo-6-(trifluoromethyl)-3-quinolinecarboxylic acid, methyl ester (3, R$^3$=CF$_3$, R$^a$=CH$_3$)

Potassium tert-butoxide (0.63 g, 5.6 mmol) was added to a stirred solution of 3-[[2-[(5-chloro-2-methoxyphenyl) carbonyl]-4-(trifluoromethyl)phenyl]amino]-3-oxopropanoic acid, methyl ester prepared in Step C (2.0 g, 4.65 mmol) in anhydrous THF (30 mL) under nitrogen. The resultant mixture was heated to reflux for 30 minutes. The reaction was allowed to cool, diluted with ether (30 mL) and then acidified with 1N HCl (20 mL). The organic layer was separated, washed with brine and then dried (Na$_2$SO$_4$). Evaporation of solvents gave a beige solid (1.94 g) which was recrystallized from EtOAc/hexanes to afford the title compound as a white solid (1.82 g, 95%): mp 214–216° C.; IR (KBr, cm$^{-1}$) 1128, 1256, 1322, 1662, 1742;

$^1$H NMR (300 MHz, CDCl$_3$): δ 3.68 (3 H, s), 3.70 (3 H, s), 6.97 (1 H, d, J=8.8 Hz), 7.20 (1 H, d, J=2.5 Hz), 7.36 (1 H, s), 7.44 (1 H, dd, J=8.8 and 2.5 Hz), 7.53 (1 H, d, J=8.6 Hz), 7.73 (1 H, d, J=8.6 Hz), 12.43 (1 H, brd s); MS m/e 412 (MH$^+$). Anal. Calcd. for C$_{19}$H$_{13}$ClF$_3$NO$_4$: C, 55.42; H, 3.18; N, 3.40. Found: C, 55.27; H, 2.94; N, 3.30.

EXAMPLE 2

4-(5-Chloro-2-methoxyphenyl)-3-(hydroxymethyl)-6-(trifluoromethyl)-2(1H)-quinolinone (4, R$^3$=CF$_3$)

A solution of diisobutyl aluminum hydride (2.16 mL of 1M in hexanes, 2.16 mmol) was added dropwise to a cold (-78° C.) stirred solution of the compound of Example 1 (0.22 g, 0.54 mmol) in anhydrous THF (10 mL). The mixture was allowed to warm to room temperature and stirred for 2 to 3 hours. Reaction mixture was cooled in an ice-bath and then carefully quenched by dropwise addition of 1N HCl (10 mL). Reaction mixture was diluted with EtOAc (20 mL) and the organic layer was separated, washed with water, brine and then dried (MgSO$_4$). Evaporation of solvents gave an off-white solid (263 mg) which was triturated with ether to afford the title compound as a white solid (178 mg, 86%): mp 232–235° C.; IR (KBr, cm$^{-1}$) 1126, 1264, 1322, 1654, 3442;

$^1$H NMR (300 MHz, CDCl$_3$): δ 3.70 (3 H, s), 4.41 (1 H, d, J=12.5 Hz), 4.53 (1 H, d, J=12.5 Hz), 7.01 (1 H, d, J=8.8 Hz), 7.15(1 H, d, J=2.6 Hz), 7.33 (1 H, s), 7.47 (1 H, dd, J=8.8 and 2.6 Hz), 7.52 (1 H, d, J=8.6 Hz), 7.71 (1 H, d, J=8.6 Hz), 12.33 (1 H, brd s); MS m/e 384 (MH$^+$). Anal. Calcd. for C$_{18}$H$_{13}$ClF$_3$NO$_3$: C, 56.34; H, 3.41; N, 3.65. Found: C, 55.72; H, 3.44; N, 3.55.

EXAMPLE 3

4-(5-Chloro-2-methoxyphenyl)-3-(hydroxymethyl)-7-(trifluoromethyl)-2(1H)-quinolinone (4, R$^3$=R$^4$=H, R$^2$=CF$_3$)

Following the general procedure described in Examples 1 and 2, the title compound was prepared.

mp 174–176° C.; MS m/e 384 (MH$^+$); $^1$H NMR (300 MHz, DMSO-d$_6$): δ 3.64 (3 H, s), 3.88 (1 H, d, J=11.0 Hz), 4.31 (1 H, d, J=11.0 Hz), 4.70 (1 H, brd s), 7.05 (1 H, d, J=8.4 Hz), 7.23 (1 H, d, J=8.9 Hz), 7.29 (1 H, d, J=2.4 Hz), 7.36 (1 H, d, J=8.4 Hz), 7.55 (1 H, dd, J=8.7 and 2.4 Hz), 7.65 (1 H, s), 12.23 (1 H, s).

EXAMPLE 4

4-(5-Chloro-2-methoxyphenyl)-1,2-dihydro-2-oxo-6-(trifluoromethyl)-3-quinolinecarboxaldehyde (5, R$^3$=CF$_3$)

Manganese dioxide (0.44 g, 5 mmol) was added to a stirred solution of the compound of Example 2 (384 mg, 1 mmol) in anhydrous CH$_2$Cl$_2$ (10 mL). Resultant suspension was stirred overnight under nitrogen. Additional MnO$_2$ (0.44 g, 5 mmol) was added and continued to stir the suspension until the oxidation is complete (2 to 3 days). The suspension was filtered through a pad of Celite, washed with additional CH$_2$Cl$_2$. Evaporation of the solvent gave the title compound as a light-yellow solid (206 mg, 54%): mp 238–240° C.; IR (KBr, cm$^{-1}$) 1120, 1268, 1320, 1678, 1707;

$^1$H NMR (300 MHz, CDCl$_3$): δ 3.71 (3 H, s), 7.01 (1 H, d, J=8.9 Hz), 7.10 (1 H, d, J=2.6 Hz), 7.48 (1 H, m), 7.51 (1 H, d, J=2.6 Hz), 7.59 (1 H, d, J=8.6 Hz), 7.82 (1 H, dd, J=8.7 and 1.8 Hz), 10.29 (1 H, s), 12.53 (1 H, brd s); MS m/e 380 (M-H)$^-$.

EXAMPLE 5

(E)-3-[4-(5-Chloro-2-methoxyphenyl)-1,2-dihydro-2-oxo-6-(trifluoromethyl)-3-quinolinyl]-2-propenoic acid, ethyl ester (6, R$^3$=CF$_3$)

To a stirred cold suspension of NaH (84 mg, 2.1 mmol, 60% in mineral oil) in anhydrous DMF (2 mL) a solution of triethyl phosphonoacetate (0.43 g, 1.95 mmol) in DMF (1 mL) was added dropwise under nitrogen. The mixture was stirred for 30 minutes and then neat 4-(5-chloro-2-methoxyphenyl)-1,2-dihydro-2-oxo-6-(trifluoromethyl)-3-quinolinecarboxaldehyde (0.60 g, 1.62 mmol) was added. Resultant mixture was allowed to warm to room temperature and stirred for 3 hours. After this period TLC shows absence of the aldehyde and formation isomeric mixture of the esters. The reaction was cooled in an ice-bath and quenched with 1N HCl. The product was extracted with 1:1 ether/EtOAc, washed with saturated NaHCO$_3$, water, brine and then dried (Na$_2$SO$_4$). Evaporation of solvents gave a beige solid (0.765 g) which was recrystallized from EtOAc/hexanes to provide the title compound as a pure trans (E) isomer (0.497 g). Concentration of mother liquor followed by trituration with ether gave additional 123 mg of the ester as a isomeric mixture. Total combined yield of the purified esters was 0.62 g (86%). Analytical data for the title compound: mp 270–273° C.;

IR (KBr, cm$^{-1}$) 1126, 1284,1322, 1664, 1713; $^1$H NMR (300 MHz, CDCl$_3$): δ 1.28 (3 H, t, J=7.1 Hz), 3.70 (3 H, s), 4.20 (2 H, q, J=7.1 Hz), 7.04 (1 H, d, J=8.9 Hz), 7.11 (1 H, d, J=2.6 Hz), 7.24–7.33 (2 H, m), 7.43 (1 H, s), 7.48–7.52 (2 H, m), 7.76 (1 H, d, J=8.6 Hz), 12.02 (1 H, brd s); MS m/e 450 (M-H)$^-$.

EXAMPLE 6

(E)-4-(5-Chloro-2-methoxyphenyl)-3-(3-hydroxy-1-propenyl)-6-(trifluoromethyl)-2(1H)-quinolinone (7, R$^3$=CF$_3$)

To a stirred cold (-78° C.) solution of the ester of the compound of Example 5 (0.3 g, 0.66 mmol) in anhydrous THF (9 mL) a Dibal-H solution in hexanes (3 mmol, 3 mL of 1M solution) was added dropwise under nitrogen. The mixture was allowed to warm to room temperature and stirred for 2 hours. The reaction mixture was cooled in ice-bath and then quenched carefully with 1N HCl (10 mL). Ethyl acetate (30 mL) was added, layers separated, washed with water, brine and then dried (MgSO$_4$). Evaporation of solvents gave a white solid (0.29 g) which was triturated with ether to afford the title compound as an alcohol (234 mg):

mp 266–268° C.; $^1$H NMR (300 MHz, DMSO-d$_6$): δ 3.67 (3 H, s), 3.96 (2 H, m), 4.76 (1 H, t, J=5.3 Hz), 6.11 (1 H, d, J=15.7 Hz), 7.01 (1 H, s), 7.18 (1 H, dt, J=15.7 and 4.6 Hz), 7.27–7.31 (2 H, m), 7.52 (1 H, d, J=8.6 Hz), 7.60 (1 H, dd, J=8.9 and 2.7 Hz), 7.79 (1 H, dd, J=8.6 and 1.8 Hz), 12.36 (1 H, s); MS m/e 408 (M-H)$^-$. Anal. Calcd. for C$_{20}$H$_{15}$ClF$_3$NO$_3$: C, 58.62; H, 3.69; N, 3.42. Found: C, 58.50; H, 3.74; N, 3.35.

EXAMPLE 7

4-(5-Chloro-2-methoxyphenyl)-1,2-dihydro-2-oxo-6-(trifluoro-methyl)-3-quinolinepropanoic acid, ethyl ester (8, R$^3$=CF$_3$)

To a solution of the ester prepared in Example 5 in ethanol and anhydrous HCl in a Parr shaker bottle, PtO$_2$ (5–10% by weight) was treated under nitrogen. The resultant suspension was hydrogenated at 60 psi overnight. The catalyst was filtered off and the filtrate was rotary evaporated to afford the title compound: mp 193–195° C.;

$^1$H NMR (300 MHz, CDCl$_3$): δ 1.16(3 H, m), 2.43(2 H, m), 2.65(2 H, m), 3.65 (3 H, s), 4.01 (2 H, m), 6.96–7.01 (2 H, m), 7.14 (1 H, s), 7.25 (2 H, s 7.40–7.43 (2 H, m), 7.60 (1 H, brd s); MS m/e 452 (M-H)$^-$.

EXAMPLE 8

4-(5-Chloro-2-methoxyphenyl)-3-(3-hydroxypropyl)-6-(trifluoromethyl)-2(1H)-quinolinone (9, R$^3$=CF$_3$)

Following the general procedure described in Example 6, the compound of Example 7 was reduced to provide the title compound.

mp 200–202° C.; $^1$H NMR (300 MHz, CDCl$_3$): δ 1.60 (2 H, m), 2.20 (3 H, brd m), 3.50 (2 H, m), 3.63 (3 H, s), 6.97 (1 H, d, J=8.8 Hz), 7.04 (1 H, d, J=2.6 Hz), 7.16 (1 H, s), 7.19 (1 H, s), 7.41 (1 H, dd, J=8.8 and 2.6 Hz), 7.49 (1 H, d, J=8.3 Hz), 7.65 (1 H, J=7.36 Hz), 12.45 (1 H, brd s); MS m/e 412 (MH)$^+$.

EXAMPLE 9

4-(5-Chloro-2-hydroxyphenyl)-3-(hydroxymethyl)-6-(trifluoromethyl)-2(1H)-quinolinone (14, R$^3$=CF$_3$)

Step A: [2-Amino-5-(trifluoromethyl)phenyl](5-chloro-2-hydroxyphenyl)methanone (10, R$^3$=CF$_3$)

To a cold solution (-78° C.) of N-[2-[(5-chloro-2-methoxyphenyl) carbonyl]-4-(trifluoromethyl) phenyl] aminocarboxylic acid, 1,1-dimethylethyl ester prepared in Example 1, Step A (7.0 g, 21.2 mmol) in methylene chloride (60 mL), 1.0 M BBr$_3$ solution in methylene chloride (46.7 mL, 46.7 mmol) was added dropwise. The resultant red solution was allowed to warm to room temperature and stirred overnight. The reaction mixture was quenched with saturated NaHCO$_3$ solution. The organic layer was separated and washed with water, brine and then dried (MgSO$_4$). Evaporation of the solvent gave a yellow-reddish solid which was recrystallized from CH$_2$Cl$_2$/hexanes to afford the title compound as a yellow solid (6.58 g, 98%).

Step B: 3-[[2-[(5-Chloro-2-hydroxyphenyl)carbonyl]-4-(trifluoromethyl)phenyl]amino]-3-oxopropanoic acid, methyl ester (11, R$^3$=CF$_3$)

To a solution of [2-amino-5-(trifluoromethyl)phenyl](5-chloro-2-hydroxyphenyl)methanone (0.5 g, 1.58 mmol) and pyridine (0.25 mL, 3.17 mmol) in methylene chloride (15 mL), a solution of methyl malonyl chloride (0.34 mL, 3.17 mmol) in methylene chloride (10 mL) was added dropwise at 0° C. The reaction mixture was then allowed to warm to room temperature and stirred for 2 hours. The reaction mixture was acidified with 1N HCl and the organic layer was separated. It was then washed with saturated NaHCO$_3$ twice, water, brine and dried (MgSO$_4$). Evaporation of the solvent gave the title compound as a yellowish oil.

Step C: 2-Chloro-6,8-dihydro-11-(trifluoromethyl)-7H-[1]benzopyrano[3,4-c]quinolin-6,7-dione (12, R$^3$=CF$_3$)

The crude 3-[[2-[(5-chloro-2-hydroxyphenyl)carbonyl]-4-(trifluoromethyl)phenyl]amino]-3-oxopropanoic acid, methyl ester prepared in Step B was dissolved in THF (15 mL) and potassium t-butoxide solution (1M in THF, 1.74 mmol, 1.74 mL) was added. The reaction mixture was heated under reflux for 15 minutes. It was then acidified with 1N HCl and the organic layer was separated. The organic layer was washed with water, brine and dried (MgSO$_4$). Evaporation of the solvent gave a yellow solid which was triturated with ethyl acetate/hexanes to afford the title compound as a yellow solid (0.48 g, 83%): mp>250° C. MS m/e 366 (MH$^+$).

Anal. Calcd. for C$_{17}$H$_7$ClF$_3$NO$_3$ •0.5H$_2$O: C, 54.49; H, 2.15; N, 3.74. Found: C, 54.10; H, 1.85; N, 3.63. $^1$H NMR (DMSO-d$_6$): δ 7.48 (d, J=8.8 Hz, 1H), 7.55 (d, J=8.5 Hz, 1H), 7.76(dd, J=8.9 Hz, 2.2 Hz, 1H), 7.98 (d, J=8.7 Hz, 1H), 8.10 (d, J=2.1 Hz, 1H), 8.42 (s, 1H). IR (KBr, cm$^{-1}$): 3479, 3074, 1761, 1652, 1630, 1577, 1368, 1325, 1141.

Step D: 4-(5-Chloro-2-hydroxyphenyl)-3-(hydroxymethyl)-6-(trifluoromethyl)-2(1H)-quinolinone (14, R$^3$=CF$_3$)

To a cold suspension (−78° C.) of 2-chloro-6,8-dihydro-11-(trifluoromethyl)-7H-[1]benzopyrano[3,4-c]quinolin-6,7-dione prepared in Step C (1.0 g, 2.73 mmol) in methylene chloride (20 mL), a solution of Dibal-H (1M in methylene chloride, 13.7 mL, 13.7 mmol) was added dropwise. The reaction mixture was warmed to 0° C. and maintained for 3 hours. The reaction mixture was acidified with 1N HCl and extracted with ethyl acetate twice. The organic layer was separated and washed with water, brine and then dried (MgSO$_4$). Evaporation of the solvent followed by recrystallization of the crude product from ethyl acetate/hexanes afforded the title compound as a white solid (0.7 g, 69%): mp>250° C.; MS m/e 368 (M−H)$^-$.

Anal. Calcd. for C$_{17}$H$_{11}$ClF$_3$NO$_3$: C, 55.23; H, 3.00; N, 3.79. Found: C, 56.59; H, 4.02; N, 3.36. $^1$H NMR (DMSO-d$_6$): δ 3.90 (dd, J=10.9 Hz, 5.3 Hz, 1H), 4.36 (dd, J=10.9 Hz, 5.6 Hz, 1H), 4.70 (t, J=5.4 Hz, 1H), 7.03 (d, J=8.7 Hz, 1H), 7.17 (s, 1H), 7.26 (d, J=2.7 Hz, 1H), 7.39 (dd, J=8.7 Hz, 2.7 Hz, 1H), 7.53 (d, J=8.6 Hz, 1H), 7.81 (dd, J=8.9 Hz, 1.9 Hz, 1H), 9.95 (s, 1H), 12.31 (s, 1H).

EXAMPLE 10

3-[4-(5-Chloro-2-hydroxyphenyl)-1,2-dihydro-2-oxo-6-(trifluoromethyl)-3-quinolinyl]-2-propenoic acid, ethyl ester (15, R$^3$=CF$_3$)

Step A: 2-Chloro-6,8-dihydro-6-hydroxy-11-(trifluoromethyl)-7H-[1]benzopyrano[3,4-c]quinolin-7-one (13, R$^3$=CF$_3$)

To a cold solution (−78° C.) of 2-chloro-6,8-dihydro-11-(trifluoromethyl)-7H-[1]benzopyrano[3,4-c]quinolin-6,7-dione prepared in Example 9, Step C (1.15 g, 3.15 mmol) in THF (30 mL), a solution of Dibal-H (1M in THF, 15.7 mL, 15.7 mmol) was added dropwise. The reaction mixture was maintained at −78° C. for 4 hours. The reaction mixture was acidified with 1N HCl and extracted with ethyl acetate twice. The organic layer was separated and washed with water, brine and then dried (MgSO$_4$). Evaporation of the solvent followed by trituration of crude product with ethyl acetate to afforded the title compound as a white solid (0.9 g, 78%): mp>260° C.; MS m/e 366 (M−H)$^-$.

Anal. Calcd. For C$_{17}$H$_9$ClF$_3$NO$_3$·0.25H$_2$O: C, 54.86; H, 2.57; N, 3.76. Found: C, 54.92; H, 2.92; N, 3.46. $^1$H NMR (DMSO-d$_6$): δ 6.40 (d, J=6.2 Hz, 1H), 7.31 (d, J=8.7 Hz, 1H), 7.55–7.63 (m, 3H), 7.94 (d, J=8.7 Hz, 1H), 8.07 (d, J=2.4 Hz, 1H), 8.38 (s, 1H), 12.44 (s, 1H). IR (KBr, cm$^{-1}$): 3300, 1669, 1631, 1605, 1575, 1326, 1279, 1133.

Step B: 3-[4-(5-Chloro-2-hydroxyphenyl)-1,2-dihydro-2-oxo-6-(trifluoromethyl)-3-quinolinyl]-2-propenoic acid, ethyl ester (15, R$^3$=CF$_3$)

To a cold suspension (0° C.) of NaH (60% in mineral oil, 41 mg, 1.0 mmol) in DMF (3 mL), triethyl phosphonoacetate (0.1 mL, 0.5 mmol) was added dropwise. The reaction mixture was stirred at 0° C. for 0.5 hours and then a solution of 2-chloro-6,8-dihydro-6-hydroxy-11-(trifluoromethyl)-7H-[1]benzopyrano[3,4-c]quinolin-7-one prepared in Example 10, Step A (0.15 g, 0.41 mmol) in DMF (5 mL) was added. The red reaction mixture was allowed to warm to room temperature and stirred for 4 hours. The reaction mixture was carefully quenched with 1N HCl solution and was extracted with ethyl acetate. The organic layer was separated and washed with saturated NaHCO$_3$, water, brine and dried (MgSO$_4$). Evaporation of the solvent followed by recrystallization from ethyl acetate/hexanes afforded the title compound as a white solid (127 mg, 72%): mp 262–268° C. (dec.); MS m/e 436 (M−H)$^-$.

Anal. Calcd. for C$_{21}$H$_{15}$ClF$_3$NO$_4$: C, 57.61; H, 3.45; N, 3.20. Found: C, 57.31; H, 3.46; N, 3.15. $^1$H NMR (DMSO-d$_6$): δ 1.18 (t, J=7.1 Hz, 3H), 4.09 (q, J=7.0 Hz, 1H), 7.08 (d, J=8.8 Hz, 1H), 7.16 (d, J=15.7 Hz, 1H), 7.20 (s, 1H), 7.29 (d, J=2.7 Hz, 1H), 7.34 (d, J=15.7 Hz, 1H), 7.48 (dd, J=8.7 Hz, 2.7 Hz, 1H), 7.57 (d, J=8.6 Hz, 1H), 7.90 (dd, J=8.8 Hz, 1.8 Hz, 1H), 10.1 (s, 1H), 12.6 (s, 1H). IR (KBr, cm$^{-1}$): 3225, 1683, 1662, 1626, 1323, 1301, 1115.

EXAMPLE 11

3-[4-(5-Chloro-2-hydroxyphenyl)-1,2-dihydro-2-oxo-6-(trifluoromethyl)-3-quinolinyl]-2-propenoic acid (16, R$^3$=CF$_3$)

To a solution of the compound of Example 10 (40 mg, 0.09 mmol) in EtOH (2 mL), 10N NaOH (1 mL) was added and the mixture was stirred at room temperature overnight. The reaction was acidified with 1N HCl and the precipitated a light yellow solid of title compound was collected (34 mg, 91% yield): mp 258–261° C.; MS m/e 408 (M−H)$^-$.

Anal. Calcd. for C$_{19}$H$_{11}$ClF$_3$NO$_4$·0.5H$_2$O: C, 52.79; H, 3.15; N, 3.24. Found: C, 52.93; H, 2.82; N, 3.10. $^1$H NMR (DMSO-d$_6$): δ 7.07–7.13 (m, 2H), 7.18 (s, 1H), 7.25–7.30 (m, 2H), 7.47 (dd, J=8.7 Hz, 2.7 Hz, 1H), 7.57 (d, J=8.7 Hz, 1H), 7.89 (dd, J=8.7 Hz, 1.7 Hz, 1H), 10.11 (s, 1H), 12.37 (s, br, 1H), 12.57 (s, 1H). IR (KBr, cm$^{-1}$): 3144, 2996, 1676, 1628, 1323, 1270, 1252, 1130.

EXAMPLE 12

4-(5-Chloro-2-hydroxyphenyl)-3-(3-hydroxy-1-propenyl)-6-(trifluoromethyl)-2(1H)-quinolinone (17, R$^3$=CF$_3$)

To a cold suspension (−78° C.) of the compound of Example 10 (0.2 g, 0.46 mmol) in methylene chloride (10 mL), a solution of Dibal-H (1M in methylene chloride, 2.3 mL, 2.3 mmol) was added dropwise. The reaction mixture was warmed to room temperature and stirred for 4 hours. The reaction mixture was acidified with 1N HCl and extracted with ethyl acetate twice. The organic layer was separated and washed with water, brine and dried (MgSO$_4$). Evaporation of the solvent followed by recrystallization from ethyl acetate/hexanes afforded the title compound as an off-white solid (0.14 g, 77%): mp 203–209° C. (dec.); MS m/e 394 (M−H)$^-$.

Anal. Calcd. for C$_{19}$H$_{13}$ClF$_3$NO$_3$·0.5H$_2$O: C, 56.38; H, 3.49; N, 3.46. Found: C, 56.35; H, 3.72; N, 3.29. $^1$H NMR (DMSO-d$_6$): δ 3.97 (dt, J=1.7 Hz, 4.9 Hz, 2H), 4.77 (t, J=5.3 Hz, 1H), 6.16 (dd, J=15.8 Hz, 1.9 Hz, 1H), 7.05 (d, J=8.7 Hz, 1H), 7.10 (s, 1H), 7.16 (d, J=2.7 Hz, 1H), 7.21 (dt, J=15.7 Hz, 4.7 Hz, 1H), 7.41 (dd, J=8.7 Hz, 2.7 Hz, 1H), 7.51 (d, J=8.5 Hz, 1H), 7.78 (dd, J=8.7 Hz, 1.8 Hz, 1H), 9.90 (s, 1H), 12.32 (s, 1H). IR (KBr, cm$^{-1}$): 3286, 1656, 1641, 1322, 1294, 1169, 1120, 1075.

EXAMPLE 13

4-(5-Chloro-2-hydroxyphenyl)-1,2-dihydro-2-oxo-6-(trifluoromethyl)-3-quinolinepropanoic acid, ethyl ester (18, R$^3$=CF$_3$)

To a solution of the compound of Example 10 (0.4 g, 0.91 mmol) in ethanol (20 mL), PtO$_2$ (38 mg) and 3 drops of 1N HCl were added. The mixture was hydrogenated in a parr apparatus at 50 psi overnight. The catalyst was filtered off by passing through a pad of Celite and washing with ethanol. The filtrate was evaporated to dryness and the white residue was flash chromatographed (silica gel, 2:1 ethyl acetate:hexanes) to afford the title compound as a white solid (0.29 g, 72%): mp 241–245° C. (dec.); MS m/e 438 (M–H)⁻.

Anal. Calcd. for $C_{21}H_{17}ClF_3NO_4$: C, 57.35; H, 3.90; N, 3.18. Found: C, 57.27; H, 4.02; N, 2.99. $^1$H NMR (CD$_3$OD): δ 1.18(t, J=7.1 Hz, 3H), 2.49–2.55 (m 2H), 2.69–2.75 (m, 2H), 4.05 (q, J=7.1 Hz, 2H), 7.02 (d, J=8.7 Hz, 1H), 7.13 (d, J=2.6 Hz, 1H), 7.26 (s, 1H), 7.38 (dd, J=8.7 Hz, 2.6 Hz, 1H), 7.51 (d, J=8.6 Hz, 1H), 7.73 (dd, J=8.6 Hz, 1.7 Hz, 1H). IR (KBr, cm$^{-1}$): 3353, 1698, 1656, 1626, 1376, 1311, 1270, 1167, 1128, 1074.

EXAMPLE 14

4-(5-Chloro-2-hydroxyphenyl)-1,2-dihydro-2-oxo-6-(trifluoromethyl)-3-quinolinepropanoic acid (19, $R^3$=CF$_3$)

To a solution of the compound of Example 13 (38 mg, 0.087 mmol) in EtOH (2 mL), 10N NaOH (1 mL) was added and the mixture was stirred at room temperature overnight. The reaction was acidified with 1N HCl and the precipitated white solid was collected to afford the title compound (30 mg, 84%): mp 255–258° C.; MS m/e 410 (M–H)⁻.

Anal. Calcd. for $C_{19}H_{13}ClF_3NO_4$•0.5H$_2$O: C, 54.24; H, 3.35; N, 3.33. Found: C, 54.10; H, 3.10; N, 3.28. $^1$H NMR (DMSO-d$_6$): δ 2.32–2.37 (m, 2H), 2.47–2.51 (m, 2H), 7.04–7.07 (m, 2H), 7.25 (d, J=2.6 Hz, 1H), 7.40 (dd, J=8.7 Hz, 2.7 Hz, 1H), 7.52 (d, J=8.6 Hz, 1H), 7.79 (dd, J=8.7 Hz, 1.9 Hz, 1H), 9.98 (s, 1H), 12.10 (s, br, 1H), 12.31 (s, 1H). IR (KBr, cm$^{-1}$): 3283, 3155, 1714, 1626, 1560, 1405, 1275, 1194, 1167, 1132.

EXAMPLE 15

4-(5-Chloro-2-hydroxyphenyl)-3-(3-hydroxypropyl)-6-(trifluoromethyl)-2(1H)-quinolinone (20, $R^3$=CF$_3$)

To a cold suspension (–78° C.) of the compound of Example 13 (0.2 g, 0.45 mmol) in methylene chloride (10 mL), a solution of Dibal-H (1M in methylene chloride, 3.7 mL, 3.7 mmol) was added dropwise. The reaction mixture was warmed to room temperature and stirred for 4 hours. The reaction mixture was acidified with 1N HCl and extracted with ethyl acetate twice. The organic layer was separated and washed with water, brine and dried (MgSO$_4$). Evaporation of the solvent followed by recrystallization from ethyl acetate/hexanes afforded the title compound as a white solid (145 mg, 80%): mp 257–259° C. (dec.); MS m/e 398 (MH$^+$).

Anal. Calcd. for $C_{19}H_{15}ClF_3NO_3$•0.67 EtOAc: C, 57.00; H, 4.49; N, 3.07. Found: C, 57.17; H, 4.62; N, 2.88. $^1$H NMR (DMSO-d$_6$): δ 1.5 (m, 2H), 2.3 (m, 2H), 3.25 (m, 2H), 4.35 (m, 1H), 7.02–7.07 (m, 2H), 7.21 (d, J=2.5 Hz, 1H), 7.39 (dd, J=8.7 Hz, 2.7 Hz, 1H), 7.51 (d, J=8.5 Hz, 1H), 7.77 (d, J=8.5 Hz, 1H), 9.90 (s, 1H), 12.24 (s, 1H). IR (KBr, cm$^{-1}$): 3315, 1654, 1624, 1569, 1324, 1273, 1125, 1073.

EXAMPLES 16 and 17

(E)- and (Z)-4-(5-Chloro-2-hydroxyphenyl)-3-(2-fluoro-3-hydroxy-1-propenyl)-6-(trifluoromethyl)-2 (1H)-quinolinone (23, $R^3$=CF$_3$) and (25, $R^3$=CF$_3$)
Step A: To a cold suspension (0° C.) of NaH (60% mineral oil, 68 mg, 1.7 mmol) in DMF (5 mL), triethyl 2-fluoro-2-phosphonoacetate (0.165 mL, 0.82 mmol) was added. The resultant mixture was stirred at 0° C. for 0.5 hours and then a solution of 2-chloro-6,8-dihydro-6-hydroxy-11-(trifluoromethyl)-7H-[1]benzopyrano[3,4-c]quinolin-7-one prepared in Example 10, Step A (0.25 g, 0.68 mmol) in DMF (5 mL) was added. The red reaction mixture was allowed to warm to room temperature and stirred for 4 hours. The reaction mixture was quenched with 1N HCl and then extracted with ethyl acetate. The organic layer was separated and washed with saturated NaHCO$_3$, water, brine and then dried (MgSO$_4$). Evaporation of the solvent gave a isomeric mixture of esters of formula (21). (E:Z=1:2.5, 224 mg, 72%) as a colorless oil.

Step B: To a cold suspension (–78° C.) of the crude esters from Step A (210 mg, 0.46 mmol) in methylene chloride (10 mL), a solution of Dibal-H (1M in methylene chloride, 3.3 mL, 3.3 mmol) was added dropwise. The reaction mixture was warned to room temperature and stirred overnight. The reaction mixture was acidified with 1N HCl and extracted with ethyl acetate twice. The organic layer was separated and washed with water, brine and then dried (MgSO$_4$). The crude isomeric alcohols were purified by column chromatography (silica gel, 2:1 ethyl acetate/hexanes) to afford individual E-isomer (E)-4-(5-chloro-2-hydroxyphenyl)-3-(2-fluoro-3-hydroxy-1-propenyl)-6-(trifluoromethyl)-2 (1H)-quinolinone Example 16 (23, $R^3$=CF$_3$) and Z-isomer (Z)-4-(5-chloro-2-hydroxyphenyl)-3-(2-fluoro-3-hydroxy-1-propenyl)-6-(trifluoromethyl)-2(1H)-quinolinone Example 17 (25, $R^3$=CF$_3$). The physical characteristics of the (E)- and (Z)-isomer compounds are described below.

EXAMPLE 16

(E)-4-(5-Chloro-2-hydroxyphenyl)-3-(2-fluoro-3-hydroxy-1-propenyl)-6-(trifluoromethyl)-2(1H)-quinolinone (23, $R^3$=CF$_3$)

mp 215–218° C. (dec.); MS m/e: 412 (M–H)⁻. Anal. Calcd. for $C_{19}H_{12}ClF_3NO_3$•0.33H$_2$O: C, 54.37; H, 3.04; N, 3.34. Found: C, 54.72; H, 3.11; N, 3.18. $^1$H NMR (DMSO-d$_6$): δ 3.64 (m, 1H), 3.83 (m, 1H), 4.99 (m, 1H), 5.61 (d, J=19.6 Hz, 1H), 7.03 (d, J=8.7 Hz, 1H), 7.20–7.23 (m, 2H), 7.38 (dd, J=8.7 Hz, 2.7 Hz, 1H), 7.54 (d, J=8.7 Hz, 1H), 7.84 (d, J=8.9 Hz, 1H), 10.09 (s, 1H), 12.42 (s, 1H).

EXAMPLE 17

(Z)-4-(5-Chloro-2-hydroxyphenyl)-3-(2-fluoro-3-hydroxy-1-propenyl)-6-(trifluoromethyl)-2(1H)-quinolinone (25, $R^3$=CF$_3$)

mp 242–245° C. (dec.); MS m/e 412 (M–H)⁻. Anal. Calcd. for $C_{19}H_{12}ClF_3NO_3$•0.33H$_2$O: C, 54.37; H, 3.04; N, 3.34. Found: C, 54.62; H, 3.27; N, 3.11. $^1$H NMR (DMSO-d$_6$): δ 3.81–3.86 (m, 2H), 5.35 (t, J=5.9 Hz, 1H), 5.57 (d, J=40.3 Hz, 1H), 7.00 (d, J=8.7 Hz, 1H), 7.12 (d, J=2.6 Hz, 1H), 7.21 (s, 1H), 7.34 (dd, J=8.7 Hz, 2.7 Hz, 1H), 7.51 (d, J=8.6 Hz, 1H), 7.81 (dd, J=8.6 Hz, 1.6 Hz, 1H), 9.90 (s, 1H), 12.32 (s, 1H).

EXAMPLES 18 and 19

Following the general procedures described for the compounds of Examples 16 and 17, the compounds of Example 18 (24, $R^3$=CF$_3$) (E-isomer) and Example 19 (26, $R^3$=CF$_3$) (Z-isomer) were prepared from the compound of formula (5) prepared in Example 4, as illustrated in Reaction Scheme 5. The physical characterizing data of the (E)- and (Z)-isomers are described below.

EXAMPLE 18

(E)-4-(5-Chloro-2-methoxyphenyl)-3-(2-fluoro-3-hydroxy-1-propenyl)-6-(trifluoromethyl)-2(1H)-quinolinone (24, $R^3$=$CF_3$)

mp 180–182° C.; MS m/e: 426 (M–H)⁻. ¹H NMR (CDCl₃): δ 3.68 (3 H, s), 4.10 (2 H, d, J=24.0 Hz), 5.54 (1 H, d, J=18.0 Hz), 7.01 (1 H, d, J=8.9 Hz), 7.04 (1 H, d, J=2.4 Hz), 7.32 (1 H, s), 7.46 (1 H, dd, J=8.9 and 2.3 Hz), 7.52 (1 H, d, J=8.5 Hz), 7.73 (1 H, d, J=7.6 Hz), 11.65 (1 H, brd s).

EXAMPLE 19

(Z)-4-(5-Chloro-2-methoxyphenyl)-3-(2-fluoro-3-hydroxy-1-propenyl)-6-(trifluoromethyl)-2(1H)-quinolinone (26, $R^3$=$CF_3$)

mp 230–232° C.; MS m/e: 426 (M–H)⁻. ¹H NMR (CDCl₃): δ 3.69(3 H, s), 4.09(2 H, d, J=10.7 Hz), 5.70(1 H, d, J=38.1 Hz), 6.98 (1 H, d, J=8.8 Hz), 7.09 (1 H, s), 7.35 (1 H, s), 7.41 (1 H, d, J=8.8 Hz), 7.50 (1 H, m), 7.67 (1 H, brd s), 11.75 (1 H, brd s).

EXAMPLE 20

4-(5-Chloro-2-hydroxyphenyl)-3-(2-hydroxyethyl)-6-(trifluoromethyl)-2(1H)-quinolinone (31a, $R^3$=$CF_3$, n=2)

Step A: 4-[[2-[(5-Chloro-2-methoxyphenyl)carbonyl]-4-(trifluoromethyl)phenyl]amino]-4-oxobutanoic acid, methyl ester (27, $R^3$=$CF_3$, $R^a$=$CH_3$, n=2)

Neat 3-carbomethoxypropionyl chloride (4.8 mL, 0.039 mol) was added to a stirred cold (0° C.) solution of aminobenzophenone 1-[2-amino-5-(trifluoromethyl)phenyl]-1'-(5-chloro-2-methoxyphenyl) methanone prepared in Example 1, Step B (7.0 g, 0.021 mol) and anhydrous pyridine (4.8 mL, 0.059 mol) in anhydrous CH₂Cl₂ (80 mL). The resultant mixture was allowed to warm to room temperature and maintained for 12 hours. The reaction was acidified with 1N HCl (50 mL). The organic layer was separated and washed consecutively with saturated NaHCO₃, water, brine and then dried (MgSO₄). Evaporation of the CH₂Cl₂ and trituration of the resulting residue afforded 7.71 g (82%) of amide of the title compound.

¹H NMR (300 MHz, CDCl₃): δ 2.7 (4 H, m), 3.06 (3H, s), 3.63 (3H, s), 6.85 (1H, d, J=8.9 Hz), 7.16 (1H, s), 7.30 (1H, d, J=2.6 Hz), 7.39 (1H, dd, J=8.8, 2.6 Hz), 7.57 (1H, s), 7.66 (1H, dd, J=8.9, 1.9 Hz), 8.79 (1H, d, J=8.8 Hz); MS m/e 444 (MH⁺)

Step B: 4-(5-Chloro-2-methoxyphenyl)-4-hydroxy-1,2,3,4-tetrahydro-2-oxo-6-(trifluoromethyl)-3-quinolineacetic acid, methyl ester (28, $R^3$=$CF_3$, $R^a$=$CH_3$, n=2)

A solution of potassium bis(trimethylsilyl)amide (0.5 M in toluene, 57 mL, 28.5 mmol) was added to a stirred cold (–78° C.) solution of 4-[[2-[(5-chloro-2-methoxyphenyl) carbonyl]-4-(trifluoromethyl)phenyl]amino]-4-oxobutanoic acid, methyl ester prepared in Step A (4.05 g, 9.1 mmol) in anhydrous THF (25 mL) and maintained at –78° C. for 3 hours. Acidic work-up with 1N HCl and followed by extraction with EtOAc afforded the crude title compound (4.05 g, 100%).

Step C: 4-(5-Chloro-2-methoxyphenyl)-1,2-dihydro-2-oxo-6-(trifluoromethyl)-3-quinolineacetic acid (29, $R^3$=$CF_3$, n=2)

A stirred suspension of crude 4-(5-chloro-2-methoxyphenyl)-4-hydroxy-1,2,3,4-tetrahydro-2-oxo-6-(trifluoromethyl)-3-quinolineacetic acid, methyl ester prepared in Step B (2 g, 4.5 mmol) in toluene (25 mL) was treated with a solution of 35% HBr in acetic acid (5 mL). The resultant mixture was heated at 85° C. overnight. The reaction mixture was evaporated to dryness and the residue was partitioned between water and EtOAc. The EtOAc extract was washed with brine and dried (MgSO₄) and then evaporated to afford the title compound (1.45 g, 78%).

Step D: 4-(5-Chloro-2-hydroxyphenyl)-1,2-dihydro-2-oxo-6-(trifluoromethyl)-3-quinolineacetic acid (30, $R^3$=$CF_3$, n=2)

A neat mixture of crude 4-(5-chloro-2-methoxyphenyl)-1,2-dihydro-2-oxo-6-(trifluoromethyl)-3-quinolineacetic acid prepared in Step C (1.45 g, 3.5 mmol) and pyridinium hydrochloride (5 g, 43.3 mmol) was heated at 185° C. for 3 hours. Reaction mixture was allowed to cool and 1N HCl was added and then extracted with EtOAc to afford the title compound (1.20 g, 86%): mp 158–160° C.;

¹H NMR (300 MHz, CD₃OD): δ 3.21 (1H, d, J=16.7 Hz), 3.60 (1H, d, J=16.7 Hz), 7.0 (1H,d, J=8.8 Hz), 7.13 (1H, d, J=2.6 Hz), 7.31 (1H, m), 7.37 (1H, dd, J=8.8, 2.6 Hz), 7.52 (1H, d, J=8.6 Hz), 7.75 (1 H, d, J=8.6 Hz); MS m/e 398 (MH⁺).

Step E: 4-(5-Chloro-2-hydroxyphenyl)-3-(2-hydroxyethyl)-6-(trifluoromethyl)-2(1H)-quinolinone (31a, $R^3$=$CF_3$, n=2)

A solution of borane-methyl sulfide complex (2M in THF, 125 mL, 0.25 mol) was added dropwise over 20 minutes to a stirred cold (–10° C.) partial solution of the acid 4-(5-chloro-2-hydroxyphenyl)-1,2-dihydro-2-oxo-6-(trifluoromethyl)-3-quinolineacetic acid prepared in Step D (20 g, 0.05 mol) in anhydrous THF (125 mL) under nitrogen. The resultant clear reaction mixture was allowed to warm to room temperature and continued to stir for 2 to 3 days (HPLC analysis shows absence of starting material). The reaction mixture was cooled in an ice-bath and then quenched with dropwise addition of 1N NaOH (125 mL)until basic and then acidified with 1N HCl. Ether (250 mL) was added and layers separated, washed with water, brine and then dried (Na₂SO₄). Evaporation of the solvents gave a brown solid (21.4 g) which was recrystallized from EtOAc-MeOH to afford 2.6 g of pure white solid as the first crop. Trituration of concentrated mother liquor with ether afforded 8.7 g of off-white solid as the second crop. The second crop was recrystallized from EtOAc-MeOH and combined with first crop to afford a total of 11.1 g of the title compound as a white solid: mp 255–256° C.;

¹H NMR (300 MHz, CD₃OD): δ 2.73 (2H, m), 3.64 (2H, t, J=7.4 Hz), 7.0 (1H, d, J=8.8 Hz), 7.15 (1H, d, J=2.6 Hz), 7.23 (1H, broad s), 7.36(1H, dd, J=8.8, 2.6 Hz), 7.48 (1H, d, J=8.6 Hz), 7.71 (1H, dd, J=8.6, 1.8 Hz); MS m/e 384 (MH⁺). Anal. Calcd. for $C_{18}H_{13}ClF_3NO_3$: C, 56.34; H, 3.41; N, 3.65. Found: C, 56.18; H, 3.58; N, 3.48.

EXAMPLE 21

4-(5-Chloro-2-methoxyphenyl)-3-(2-hydroxyethyl)-6-trifluoromethyl-2(1H)-quinolinone (31b, $R^3$=$CF_3$, n=2)

The compound of Example 20, Step C was reacted by the general procedure described in Example 20, Step E to afford the title compound.

mp 219–221° C.; ¹H (300 MHz, CDCl₃): δ 7.71 (1 H, d, J=8.4 Hz), 7.53–7.46 (m, 2H), 7.23 (1H, s), 7.11 (d, 1H, J=2.7 Hz), 7.02 (d, 1H, J=8.7 Hz), 3.79 (m, 2H), 3.70 (s, 3H), 3.79 (t, 2H); MS m/e 397 (MH⁺). Anal. Calcd. for $C_{19}H_{15}ClF_3NO_3$: C, 57.37, H, 3.80, N, 3.52. Found: C, 57.31, H, 3.94, N, 3.38.

EXAMPLES 22–33

General Procedure for the Preparation of Compounds of Formulas (34) and (35)

Step A: Acylation of aminobenzophenone of formula (1).

Neat acyl chloride (1.2 equivalent) was added to a stirred cold (0° C.) solution of aminobenzophenone of formula (1) (1 equivalent) and anhydrous pyridine (1.3 equivalent) in anhydrous $CH_2Cl_2$. The resultant mixture was allowed to warm to room temperature and maintained for 2 to 3 hours. The reaction was acidified with 1N HCl, layers separated and the organic layer washed with saturated $NaHCO_3$, water, brine and then dried ($MgSO_4$). Evaporation of the $CH_2Cl_2$ afforded the corresponding amide of general formula (32).

Step B: Cyclization of the amide of formula (32).

A solution of potassium bis(trimethylsilyl)amide (0.5 M in toluene, 3 equivalent) was added to a stirred cold (−78° C.) solution of the amide of formula (32) (1 equivalent) in anhydrous THF and maintained at −78° C. for 3 hours. Acidic work-up with 1N HCl and followed by extraction with EtOAc afforded the quinoline of formula (33).

Step C: Dehydration of the quinoline of formula (33).

A stirred suspension of crude compound of the formula (33) in toluene was treated with a solution of 35% HBr in acetic acid. The resultant mixture was heated at 85° C. overnight. The reaction mixture was evaporated to dryness and the residue was partitioned between water and EtOAc. The EtOAc extract was washed with brine and dried ($MgSO_4$) and then evaporated to afford the quinoline of formula (34).

Step D: Demethylation of the compound of formula (34).

A neat mixture of crude quinoline of formula (34) (1 equivalent) and pyridinium hydrochloride (5 equivalent) was heated at 185° C. for 3 hours. The reaction mixture was allowed to cool and 1N HCl was added and then extracted with EtOAc to afford the corresponding hydroxy compound of formula (35).

EXAMPLE 22

4-(5-Chloro-2-methoxyphenyl)-3-(4-methoxyphenyl)-6-trifluoromethyl-2(1H)-quinolinone (34a, $R^3=CF_3$, $R^8=$4-methoxyphenyl, n=0)

mp 130–135° C.; $^1$H NMR (300 MHz, $CDCl_3$): δ 7.62 (1H, d, J=8.7 Hz), 7.36–7.25 (3H, m), 7.10 (2H, d, J=8.7 Hz), 6.93(1H, d, J=2.7 Hz), 6.81(1 H, d, J=8.7 Hz), 6.77(2H, d, J=8.7 Hz), 3.77(s, 3H), 3.62(s, 3H); MS m/e 459 (MH$^+$). Anal. Calcd. for $C_{24}H_{17}ClF_3NO_3$: C, 62.69, H, 3.73, N, 3.05. Found: C, 62.74, H, 3.92, N, 2.89.

EXAMPLE 23

4-(5-Chloro-2-methoxyphenyl)-3-[(4-methoxyphenyl)methyl]-6-(trifluoromethyl)-2(1H)-quinolinone (34b, $R^3=CF_3$, $R^8=$4-methoxyphenyl, n=1)

mp 110–114° C.; $^1$H NMR (300 MHz, $CDCl_3$): δ 7.62 (1H, d, J=8.7 Hz), 7.47–7.43 (1H, dd, J=2.7 Hz and 8.7 Hz), 7.29 (d, 1H, J=2.7 Hz), 7.23 (s, 1H), 7.00–6.92 (m, 3H), 6.70 (d, 1H, J=8.7 Hz), 3.78 (dd, 2H), 3.72 (s, 3H), 3.57 (s, 3H); MS m/e 473 (MH$^+$).

EXAMPLE 24

4-(5-Chloro-2-methoxyphenyl)-3-(4-nitrophenyl)-6-(trifluoromethyl)-2(1H)-quinolinone (34c, $R^3=CF_3$, $R^8=$4-nitrophenyl, n=0)

mp 218–22° C.; $^1$H (300 MHz, $CDCl_3$): δ 8.12 (2H, d, J=8.7 Hz), 7.72 (1H, d, J=8.7 Hz), 7.43–7.36(m, 4H), 7.33–7.29(dd, 1H, J=2.7 and 8.7 Hz), 6.95 (d, 1H, J=2.7 Hz), 6.82 (d, 1H, J=8.7 Hz); MS m/e 474 (MH$^+$). Anal. Calcd. for $C_{23}H_{14}ClF_3N_2O_4$: C, 58.18, H, 2.97, N, 5.90. Found: C, 57.70, H, 3.20, N, 5.65.

EXAMPLE 25

4-(5-Chloro-2-methoxyphenyl)-3-(4-aminophenyl)-6-(trifluoromethyl)-2(1H)-quinolinone (34d, $R^3=CF_3$, $R^8=$4-aminophenyl, n=0)

mp 287° C.; $^1$H (300 MHz, $CDCl_3$): δ 7.62 (1H, d, J=8.4 Hz), 7.44 (1H, d, J=8.4 Hz), 7.31 (s, 1H), 7.27–7.23 (m, 4H), 6.94–6.79 (dd, 1H, J=3.6 and 8.7 Hz), 6.82 (s, 1H), 6.52 (d, 1H, J=8.7 Hz); MS m/e 444 (MH$^+$). Anal. Calcd. for $C_{23}H_{16}ClF_3NO_2$: C, 62.10, H, 3.63, N, 6.30. Found: C, 61.89, H, 3.81, N, 6.06.

EXAMPLE 26

4-(5-Chloro-2-methoxyphenyl)-3-methyl-6-trifluoromethyl-2(1H)-quinolinone (34e, n=0, $R^8=$Me, $R^3=CF_3$)

A solution of the corresponding compound of formula (33) (5.63 mmol), 33% HBr in AcOH (38.3 mmol) and 10 mL of AcOH was heated to 75° C. for 3 hours. The solution was cooled to room temperature and quenched with $H_2O$ (50 mL) and then agitated for 12 hours. The precipitate was filtered, washed with $H_2O$, and dried in vacuo. The pale brown solid was recrystallized from ethyl acetate/hexane to give the title compound as a white solid (0.550 g, 27% yield).

$^1$H NMR (300 MHz, $CDCl_3$): δ 2.04 (s, 3H), 3.72 (s, 3H), 7.03 (d, 1H, J=9.0 Hz), 7.12 (s, 1H), 7.44 (m, 3H), 7.65 (d, 1H, J=8.4 Hz), 10.93 (br s, 1H); MS m/e 368 (MH$^+$); Anal. Calcd. for $C_{18}H_{13}ClF_3NO_2$•0.33 $H_2O$: C, 58.79; H, 3.56; N, 3.81. Found: C, 58.89; H, 3.82; N, 3.53.

EXAMPLE 27

4-(5-Chloro-2-hydroxyphenyl)-3-(3,4-dimethoxyphenyl)-6-(trifluoromethyl)-2(1H)-quinolinone (35a, $R^3=CF_3$, $R^8=$3,4-dimethoxyphenyl, n=0)

mp 140–142° C.; 1 H NMR (300 MHz, $CDCl_3$): δ 7.65 (1H, d, J=8.7 Hz), 7.37 (1H, d, J=8.7 Hz), 7.35 (1H, s), 7.29–7.25(1H, dd, J=2.7 Hz and J=8.7 Hz), 6.96(1H, d, J=2.4 Hz), 6.87–6.76(2H, m), 6.63(1H, d, J=1.8 Hz), 3.85(s, 3H), 3.69(s, 3H), 3.62(3H, s); MS m/e 489 (MH$^+$). Anal. Calcd. for $C_{25}H_{19}ClF_3NO_4$: C, 61.30, H, 3.91, N, 2.86. Found: C, 61.42, H, 3.89, N, 2.75.

EXAMPLE 28

4-(5-Chloro-2-hydroxyphenyl)-3-(2,4-dihydroxyphenyl)-6-(trifluoromethyl)-2(1H)-quinolinone (35b, $R^3=CF_3$, $R^8=$2,4-dihydroxyphenyl, n=0)

mp 295° C.(dec.); $^1$H NMR (300 MHz, $CD_3OD$): δ 7.73 (1H, d, J=8.7 Hz), 7.49(1H, d, J=8.7 Hz), 7.31–7.27 (2H, dd, J=2.7 and J=8.7 Hz), 7.03–7.00(2H, m), 6.89(1H, d, J=8.7 Hz), 6.53–6.49(2H, m); MS m/e 462 (MH$^+$). Anal. Calcd. for $C_{22}H_{13}ClF_3NO_4$: C, 59.01, H, 2.93, N, 3.13. Found: C, 58.38, H, 3.15, N, 2.96.

EXAMPLE 29

4-(5-Chloro-2-hydroxyphenyl)-3-(4-hydroxyphenyl)-6-(trifluoromethyl)-2(1H)-quinolinone (35c, $R^3=CF_3$, $R^8=$4-hydroxyphenyl, n=0)

mp 220–240° C.; $^1$H NMR (300 MHz, $CDCl_3$): δ 7.53 (1H, d, J=8.7 Hz), 7.20 (1H, d, J=8.7 Hz), 7.24–7.17 (2H, m), 6.97–6.88(4H, dd, J=8.7 and 1.9 Hz), 6.81 (1H, d, J=8.7 Hz), 6.77 (2H, d, J=8.7 Hz), 3.77 (s, 3H), 3.62 (s, 3H); MS m/e 459 (MH$^+$).

EXAMPLE 30

4-(5-Chloro-2-hydroxyphenyl)-3-[(4-hydroxyphenyl)methyl]-6-(trifluoromethyl)-2(1H)-quinolinone (35d, R$^3$=CF$_3$, R$^8$=4-hydroxyphenyl, n=1)

mp 242–250° C.; $^1$H NMR (300 MHz, CD$_3$OD): δ 7.73 (1H, d, J=8.7 Hz), 7.70 (1H, d, J=8.7 Hz), 7.50 (d, 1H, J=8.7 Hz), 7.42–7.27(m, 2H), 6.70–6.87(m, 2H), 6.82 (d, 2H, J=8.7 Hz), 6.56(d, 2H, J=8.1 Hz), 3.91–3.51(2H, dd, J=13.8 and 14.7 Hz); MS m/e 445 (MH$^+$). Anal. Calcd. for C$_{23}$H$_{15}$ClF$_3$NO$_3$·0.5H$_2$O: C, 60.68, H, 3.52, N, 3.08. Found: C, 60.71, H, 3.91, N, 2.82.

EXAMPLE 31

4-(5-Chloro-2-hydroxyphenyl)-3-(4-acetamidophenyl)-6-(trifluoromethyl)-2(1H)-quinolinone (35e, R$^3$=CF$_3$, R$^8$=4-acetamidophenyl, n=0)

mp 240–260° C.; $^1$H (300 MHz, CD$_3$OD): δ 7.77 (1H, d, J=8.7 Hz), 7.55 (1H, d, J=8.7 Hz), 7.48–7.38 (m, 3H), 7.19–7.15 (m, 3H), 6.87–6.83 (m, 2H), 2.09 (s, 3H); MS m/e 472 (MH$^+$). Anal. Calcd. for C$_{24}$H$_{16}$ClF$_3$N$_3$O$_3$: C, 56.59, H, 3.93, N, 5.50. Found: C, 57.21, H, 3.73, N, 5.28.

EXAMPLE 32

4-(5-Chloro-2-hydroxyphenyl)-3-(4-aminophenyl)-6-(trifluoromethyl)-2(1H)-quinolinone (35f, R$^3$=CF$_3$, R$^8$=4-aminophenyl, n=0)

mp 222–224° C.; $^1$H (300 MHz, CD$_3$OD): δ 7.74 (1H, d, J=8.4 Hz), 7.53 (1H, d, J=8.4 Hz), 7.36 (s, 1H), 7.15 (dd, 1H, J=2.7 and Hz), 6.99 (d, J=8.4 Hz, 2H), 6.85–6.81 (m, 2H), 6.58 (1H, d, J=8.4 Hz); MS m/e 446.8 (MH$^+$). Anal. Calcd. for C$_{22}$H$_{14}$ClF$_3$N$_2$)$_3$: C, 59.14, H, 3.16, N, 6.27. Found: C, 60.27, H, 3.52, N, 6.32.

EXAMPLE 33

4-(5-Chloro-2-hydroxyphenyl)-3-[2-(4-hydroxyphenyl)ethyl]-6-(trifluoromethyl)-2(1H)-quinolinone (35g, R$^3$=CF$_3$, R$^8$=4-hydroxyphenyl, n=2)

mp 205–207° C.; $^1$H (300 MHz, CD$_3$OD): δ 7.73–7.69 (1H, dd, J=1.8 and 8.7 Hz), 7.52 (1H, d, J=8.7 Hz), 7.38–7.35(dd, 1H, J=2.7 and 6.2 Hz), 7.23 (1H, s), 7.01 (d, 1H, J=8.7 Hz), 6.78–6.60(2H, dd, J=8.7 and 7.3 Hz), 2.68 (m, 4H); MS m/e 459 (MH$^+$). Anal. Calcd. forC$_{24}$H$_{17}$ClF$_3$NO$_3$·1.5H$_2$O: C, 59.16, H, 4.11, N, 2.88. Found: C, 58.71, H, 3.78, N, 2.86.

EXAMPLE 34

4-(5-Chloro-2-hydroxyphenyl)-3-methyl-6-(trifluoromethyl)-2(1H)-quinolinone (35h, n=0, R$^8$=Me, R$^3$=CF$_3$)

MS m/z: 352 (MH$^-$); IR (KBr) 3183, 1655, 1321, 1263, 1122 cm$^{-1}$; $^1$H NMR (DMSO-d$_6$): δ 1.86 (3H, s), 7.04 (1H, d, J=8.8 Hz), 7.12 (1H, s), 7.22 (1H, d, J=2.6 Hz)), 7.39 (1H, dd, J=2.6, 8,7 Hz), 7.52 (1H, d, J=8.6 Hz), 7.78 (1H, d, J=8.7 Hz), 9.92 (1H, s), 12.26 (1H, s); Anal. Calcd. for C$_{17}$H$_{11}$ClF$_3$NO$_2$·0.5 H$_2$O: C, 56.26; H, 3.33; N, 3.86. Found: C, 56.57; H, 3.16; N, 3.81.

EXAMPLE 35

3-[4-(5-Chloro-2-hydroxyphenyl)-1,2-dihydro-2-oxo-6-(trifluoromethyl)quinolin-3-yl]acrylonitrile (36a, R=H, X=CN, R$^3$=CF$_3$)

To a cold suspension (0° C.) of NaH (60% mineral oil, 33 mg, 0.82 mmol) in DMF (5 mL), diethyl cynomethylphosphonate (63 μL, 0.39 mmol) was added dropwise. The reaction mixture was stirred at 0° C. for 0.5 hours and a solution of 2-chloro-6,8-dihydro-6-hydroxy-11-(trifluoromethyl)-7H-[1]benzopyrano[3,4-c]quinolin-7-one prepared in Example 10, Step A (120 mg, 0.33 mmol) in DMF (5 mL) was added. The red reaction mixture was allowed to warm to room temperature and stirred for 2 hours. The reaction mixture was quenched with 1N HCl and then extracted with ethyl acetate. The organic layer was separated and washed with saturated NaHCO$_3$, water, brine and then dried (MgSO$_4$). Evaporation of the solvent gave a yellowish oil which was then purified by column chromatography (silica gel, 1:1 ethyl acetate/hexanes) to afford the title compound as a yellow solid (71 mg, 56%):

mp>265° C.; MS m/e 389 (M–H)$^-$. Anal. Calcd. for C$_{19}$H$_{10}$ClF$_3$N$_2$O$_2$: C, 58.40; H, 2.58; N, 7.17. Found: C, 58.16; H, 2.81; N, 6.87. $^1$H NMR (DMSO-d$_6$): δ 6.85 (d, J=16.4 Hz, 1H), 7.10 (d, J=8.8 Hz, 1H), 7.21 (s, 1H), 7.23 (d, J=16.4 Hz, 1H), 7.30 (d, J=2.7 Hz, 1H), 7.49 (dd, J=8.8 Hz, 2.7 Hz, 1H), 7.59 (d, J=8.6 Hz, 1H), 7.93 (dd, J=8.7 Hz, 1.7 Hz, 1H), 10.19 (s, 1H), 12.70 (s, 1H). IR (KBr, cm$^{-1}$): 3333, 2224, 1656, 1625, 1585, 1321, 1265, 1118,1073.

EXAMPLE 36

3-[4-(5-Chloro-2-methoxyphenyl)-1,2-dihydro-2-oxo-6-(trifluoromethyl)quinolin-3-yl]acrylonitrile (36b, R=Me, X=CN, R$^3$=CF$_3$)

The title compound was prepared from the compound of the formula (5) prepared in Example 4 following the general procedure described in Example 35.

mp>250° C. ; MS m/e 403 (M–H)$^-$. $^1$H NMR (DMSO-d$_6$): δ 3.71 (3 H, s), 6.92 (1 H, d, J=16.3 Hz), 7.08 (2 H, m), 7.31 (1 H, s), 7.32 (1 H, d, J=16.3 Hz), 7.54 (2 H, m), 7.81 (1 H, dd, J=8.5 & 1.6 Hz), 12.41 (1 H, brd s). IR (KBr, cm$^{-1}$): 2216, 1665, 1321, 1127.

EXAMPLE 37(a)

4-[4-(5-Chloro-2-hydroxyphenyl)-1,2-dihydro-2-oxo-6-(trifluoromethyl)quinolin-3-yl]-3-buten-2-one (37a, R=H, X=Ac, R$^3$=CF$_3$)

The title compound was prepared from compound 13 prepared in Example 10, Step A by following the general procedure described in Example 35.

mp 186–188° C. MS m/e: 406 (M–H)$^-$. IR (KBr, cm$^{-1}$): 3185, 1656, 1629, 1322, 1284, 1169, 1125, 1076 Anal. Calcd. for C$_{20}$H$_{13}$ClF$_3$NO$_3$: C, 58.91; H, 3.21; N, 3.43. Found: C, 58.64; H, 3.05; N, 3.23.

EXAMPLE 37(b)

4-[4-(5-Chloro-2-methoxyphenyl)-1,2-dihydro-2-oxo-6-(trifluoromethyl)quinolin-3-yl]-3-buten-2-one (37b, R=Me, X=Ac, R$^3$=CF$_3$)

The title compound was prepared from compound 5 prepared in Example 4 by following the general procedure described in Example 5.

mp 232–234° C. MS m/e: 422 (MH$^+$). IR (KBr, cm$^{-1}$): 2844, 1686, 1625, 1656, 1588, 1320. Anal. Calcd. for $C_{21}H_{15}ClF_3NO_3$: C, 59.80; H, 3.58; N, 3.32. Found: C, 59.60; H, 3.56; N, 3.22.

EXAMPLE 38

4-(5-Chloro-2-hydroxyphenyl)-1,2-dihydro-2-oxo-6-(trifluoromethyl)-3-quinolinecarboxaldehyde oxime (38a, R=H, R$^3$=CF$_3$)

To a suspension of 2-chloro-6,8-dihydro-6-hydroxy-11-(trifluoromethyl)-7H-[1]benzopyrano[3,4-c]quinolin-7-one prepared in Example 10, Step A (41 mg, 0.11 mmol) in THF (10 mL), hydroxylamine hydrochloride (9.3 mg, 0.13 mmol) and triethylamine (0.038 mL, 0.28 mmol) were added. The reaction mixture was stirred at room temperature overnight. The THF was evaporated and water was added. The light yellow precipitate was collected and air dried to afford the title compound (36 mg, 85%): mp 195–198° C. (dec.);

MS m/e 383 (MH$^+$). Anal. Calcd. for $C_{17}H_{10}ClF_3N_2O_3$: C, 53.35; H, 2.63; N, 7.32. Found: C, 53.18; H, 4.55; N, 6.87. $^1$H NMR (DMSO-d$_6$): δ 6.98 (d, J=8.8 Hz, 1H), 7.19–7.20 (m, 2H), 7.34 (m, 1H), 7.54 (d, J=8.6 Hz, 1H), 7.85 (m, 1H), 7.95 (s, 1H), 9.87 (s, br, 1H), 11.30 (s, 1H), 12.46 (s, br, 1H). IR (KBr, cm$^{-1}$): 3247, 1661, 1629, 1322, 1265, 1168, 1121, 1076.

EXAMPLE 39

4-(5-Chloro-2-methoxyphenyl)-1,2-dihydro-2-oxo-6-(trifluoromethyl)-3-quinolinecarboxaldehyde oxime (38b, R=Me, R$^3$=CF$_3$)

A stirred suspension of the compound prepared in Example 4 (80 mg, 0.21 mmol), NH$_2$OH.HCl (18 mg, 0.25 mmol) and anhydrous NaOAc (20 mg, 0.25 mmol) in absolute ethanol (2 mL) was heated at reflux for 1 hour. The ethanol was rotary evaporated and the residue was partitioned between EtOAc and water. The EtOAc layer was separated and washed with water, brine and then dried (Na$_2$SO$_4$). Evaporation of EtOAc followed by trituration of the crude product with ether gave the title compound as a white solid (56 mg): mp 255–258° C.; IR (KBr, cm$^{-1}$) 3207, 1669, 1323, 1267, 1122;

$^1$H NMR (DMSO-d$_6$): δ 3.66 (3 H, s), 7.08 (1H, s), 7.22 (1H, d, J=8.9 Hz), 7.28 (1 H, d, J=2.6 Hz), 7.53 (2 H, dd, J=8.9 and 2.8 Hz), 7.85 (1 H, dd, J=8.7 and 1.7 Hz), 7.97 (1 H, s), 11.29 (1 H, s), 12.50 (1 H, brd s): MS 397 (MH$^+$).

EXAMPLE 40

4-(5-Chloro-2-hydroxyphenyl)-1,2-dihydro-2-oxo-6-(trifluoromethyl)-3-quinolineacetic acid, methyl ester (30b, R$^a$=Me, R$^3$=CF$_3$)

Step A: 2-Chloro-7,9-dihydro-12-(trifluoromethyl)-[1]benzoxepino[4,5-c]quinolin-6,8-dione (39, R$^3$=CF$_3$)

A stirred mixture of the carboxylic acid of the formula (30a, R$^a$=H, R$^3$=CF$_3$) (1.20 g, 3.0 mmol) and a catalytic amount of p-TsOH was refluxed in toluene for 4 hours. The solvent was removed by rotary evaporation. The residue was treated with a saturated solution of sodium bicarbonate and extracted with EtOAc. The organic extracts were dried over MgSO$_4$ and concentrated to give the title lactone compound (783 mg, 69%):

$^1$H NMR (300 MHz, DMSO-d$_6$): δ 3.23 (1H, d, J=13.3 Hz), 4.26 (1H, d, J=13.3 Hz), 7.52 (1H, d, J=8.8 Hz), 7.60 (1H, m), 7.76 (1H, dd, J=8.8, 2.6 Hz), 7.87 (1H, d, J=2.6 Hz), 7.92 (2H, d), 12.62 (1H, brd); MS m/e 380 (MH$^+$).

Step B: 4-(5-Chloro-2-hydroxyphenyl)-1,2-dihydro-2-oxo-6-(trifluoromethyl)-3-quinolineacetic acid, methyl ester (30b, R$^a$=Me, R$^8$=CF$_3$)

On attempted purification of the lactone 2-chloro-7,9-dihydro-12-(trifluoromethyl)-[1]benzoxepino[4,5-c]quinolin-6,8-dione prepared in Step A, by column chromatography on silica gel using a mixture of CH$_2$Cl$_2$-MeOH as eluant gave the ester of the title compound.

$^1$H NMR (300 MHz, DMSO-d$_6$): δ 3.17 (1H, d, J=16.4 Hz), 3.47 (1H, d, J=16.4 Hz), 3.53 (3H,s), 7.05 (1H, d, J=8.7 Hz), 7.11 (1H, d, J=2,7 Hz), 7.18 (1H, m), 7.42 (1H, dd, J=8.7, 2.7 Hz), 7.55 (1H, d, J=8.5 Hz), 7.84 (1H, dd, 8.7, 2.7 Hz), 10.0 (1H, s), 12.4 (1H, brd s); MS m/e 412 (MH$^+$).

EXAMPLE 41

4-(5-Chloro-2-hydroxyphenyl)-3-(2-hydroxy-2-methylpropyl)-6-(trifluoromethyl)-2(1H)-quinolinone (40, R=R$^1$=Me, R$^3$=CF$_3$)

A solution of methyl lithium (1M in THF, 1.6 mL, 1.6 mmol) was added to a cold (−78° C.) stirred solution of 2-chloro-7,9-dihydro-12-(trifluoromethyl)-[1]benzoxepino[4,5-c]quinolin-6,8-dione prepared in Example 40, Step A (16 mg, 0.3 mmol) in anhydrous THF (3 mL) under nitrogen. After stirring for 1 hour at −78° C., the cold bath was removed and stirring was continued for 16 hours. The reaction was quenched with 1N HCl and then extracted with EtOAc. The crude product was purified by flash chromatography (silica gel, 19:1 CH$_2$Cl$_2$/MeOH) to afford the title compound (21 mg) as a beige solid:

MS m/z: 412 (MH$^+$); $^1$H NMR (DMSO-d$_6$): δ 0.95 (6H,s), 2.6 (2H, dd), 7.0 (1H, d), 7.1 (1H, s), 7.2 (1H, s), 7.39 (1H, d), 7.55 (1H, d), 7.8 (1H, d), 9.95 (1H, s), 12.5 (1H, s).

EXAMPLE 42

4-(5-Chloro-2-hydroxyphenyl)-1-methyl-3-(2-hydroxyethyl)-6-trifluoromethyl)-2(1H)-quinolinone (43, R$^3$=CF$_3$)

Step A: 4-(5-Chloro-2-hydroxyphenyl)-3-(2-triisopropylsilyloxyethyl)-6-trifluoromethyl)-2(1H)-quinolinone (41, R$^3$=CF$_3$)

Neat triisopropylsilyl chloride (0.293 mL, 1.37 mmol, 1.05 equivalent) was added to a stirred solution of the compound of Example 20 and imidazole (0.134 g, 1.97 mmol, 1.5 equivalent) in anhydrous DMF (10 mL). After 12 hours at room temperature, the resulting mixture was poured into aqueous 1 N HCl (50 mL). The aqueous layer was extracted with ethyl acetate (3×50 ml). The combined organic layers were washed with brine (25 mL), dried (MgSO$_4$), filtered and concentrated in vacuo. The crude residue was purified using silica gel column chromatography (3:1–2:1 hexane/ethyl acetate) to afford 0.357 g of a clear viscous oil (50% yield). An analytical sample of the title compound was obtained by crystallization from ethyl acetate/hexane: mp 209–210° C.

$^1$H NMR (300 MHz, DMSO-d$_6$): δ 0.91 (21 H, s), 2.58 (2H, m), 3.63 (2H, m), 7.04 (1H, d, J=8.8), 7.06 (1H, s), 7.23 (1H, d, J=2.6), 7.40 (1H, dd, J=8.7, 2.3), 7.51 (1H, d, J=8.6), 7.78 (1H, dd, J=8.6, 1.7), 9.92 (1H, s) 12.26 (1H, s); MS m/e 540 (MH$^+$).

Step B: 4-(5-Chloro-2-hydroxyphenyl)-1-methyl-3-(2-triisopropylsilyloxyethyl)-6-trifluoromethyl)-2(1H)-quinolinone (42, R$^3$=CF$_3$)

n-Butyl lithium (0.593 mL, 0.950 mmol, 2.1 equivalent, 1.6 M/hexane) was added to a stirred solution of the quinolinone from Step A (0.244 g, 0.453 mmol) in THF at −78°

C. After 15 minutes neat iodomethane was added and the resulting mixture was allowed to warm to room temperature. After stirring for 12 hours, the reaction was quenched with aqueous 1 N HCl (10 mL) and poured into H$_2$O (50 mL). The aqueous layer was extracted with ethyl acetate (3×50 ml). The combined organic layers were washed with brine (25 mL), dried (MgSO$_4$), filtered and concentrated in vacuo. The crude residue was purified using silica gel column chromatography (4:1–3:1 hexane/ethyl acetate) to afford 0.202 g of the title compound as a white solid (81% yield).

$^1$H NMR (300 MHz, DMSO-d$_6$): δ 0.92 (21H, s), 2.63 (2H, m), 3.66 (2H, t, J=7.4), 3.75 (3H, s), 7.05 (1H, d, J=8.8), 7.15 (1H, s), 7.24 (1H, d, J=2.7), 7.41 (1H, dd, J=8.7, 2.6), 7.78 (1H, d, J=8.9), 7.91 (1H, dd, J=9.0, 1.9), 9.95 (1H, s).

Step C: 4-(5-Chloro-2-hydroxyphenyl)-1-methyl-3-(2-hydroxyethyl)-6-trifluoromethyl)-2(1H)-quinolinone (43, R$^3$=CF$_3$)

Tetrabutylammonium flouride (0.380 mL, 0.308 mmol, 2 equivalent, 1.0 M/THF) was added to a stirred solution of the quinolinone from Step B (0.105 g, 0.190 mmol) in THF (10 mL). After 12 hours, the crude reaction mixture poured into H$_2$O (50 mL). The aqueous layer was extracted with ethyl acetate (3×50 ml). The combined organic layers were washed with brine (25 mL), dried (MgSO$_4$), filtered and concentrated in vacuo. The crude residue was purified using column chromatography (silica gel, 2.5% methanol/chloroform) to afford 74 mg of a white solid. The solid was recrystallized from ethyl acetate/hexane to provide 0.064 g (86% yield) of the title compound: mp 229–230° C. $^1$H NMR (300 MHz, DMSO-d$_6$): δ 2.56 (2H, m), 3.40 (2H, m), 3.75 (3H, s), 4.57 (1 H, m), 7.05 (1H, d, J=8.8), 7.14 (1H, s), 7.25 (1H, d, J=2.6), 7.41 (1H, dd, J=8.7, 2.7), 7.77 (1H, d, J=8.8), 7.89 (1H, dd, J=8.8, 2.0), 9.91 (1H, s); MS m/e 398 (MH$^+$); Anal. Calcd. for C$_{19}$H$_{15}$ClF$_3$NO$_3$: C, 57.37; H, 3.80; N, 3.52. Found: C, 57.69; H, 3.88; N, 3.28.

EXAMPLE 43

4-(5-Chloro-2-methoxyphenyl)-1-methyl-3-(2-hydroxyethyl)-6-trifluoromethyl)-2(1H)-quinolinone (44, R$^3$=CF$_3$)

A mixture of the quinolinone compound prepared in Example 42, Step B (0.202 g, 0.365 mmol), dimethylsulfate (0.038 mL, 0.402 mmol, 1.1 equivalent), and potassium carbonate (0.056 g, 0.402 mmol, 1.1 equivalent) in acetone (15 mL) was heated at reflux for 3 hours. The resulting mixture was poured into H$_2$O (25 mL). The aqueous layer was extracted with ethyl acetate (3×50 ml). The combined organic layers were washed with brine (25 mL), dried (MgSO$_4$), filtered and concentrated in vacuo. The crude silylated quinolinone (0.228 g) was used in the subsequent reaction without purification or characterization.

Tetrabutylammonium flouride (0.802 mL, 0.802 mmol, 2 equivalent, 1.0 M/THF) was added to a stirred solution of the silylated quinolinone (0.228 g, 0.401 mmol) in THF (10 mL). After 12 hours, the crude reaction mixture poured into H$_2$O (50 mL). The aqueous layer was extracted with ethyl acetate (3×50 ml). The combined organic layers were washed with brine (25 mL), dried (MgSO$_4$), filtered and concentrated in vacuo. The crude residue was purified using column chromatography (silica gel, 1:1–1:2 hexane/ethyl acetate) to afford 0.148 g of a white solid. The solid was recrystallized from ethyl acetate/hexane to provide 0.139 g (84% yield) of the title compound: mp 175–176° C.

$^1$ H NMR (300 MHz, DMSO-d$_6$): δ 2.48 (2H, m), 3.37 (2H, m), 3.67 (3H, s), 3.75 (3H, s), 4.57 (1H, t, 5.4), 7.06 (1H, s), 7.29 (1H, d, J=9.0), 7.35 (1H, d, J=1.3), 7.61 (1H, dd, J=8.8,2.7), 7.77 (1H, d, J=8.8), 7.89 (1H, dd, J=8.8,1.9); MS m/e 412 (MH$^+$); Anal. Calcd. for C$_{20}$H$_{17}$ClF$_3$NO$_3$: C, 58.33; H, 4.16; N, 3.40. Found: C, 58.30; H, 4.07; N, 3.18.

EXAMPLE 44

4-(5-Chloro-2-hydroxyphenyl)-1-methyl-3-(2-hydroxyethyl)-6-trifluoromethyl)-2(1H)-quinolinone (43, R$^3$=CF$_3$)

Step A: 4-(5-Chloro-2-hydroxyphenyl)-3-(2-triisopropylsilyloxyethyl)-6-trifluoromethyl)-2(1H)-quinolinone (41, R$^3$=CF$_3$)

Neat triisopropylsilyl chloride (0.293 mL, 1.37 mmol, 1.05 equivalent) was added to a stirred solution of the quinolone 31a prepared in Example 20 and imidazole (0.134 g, 1.97 mmol, 1.5 equivalent) in anhydrous DMF (10 mL). After 12 hours at room temperature, the resulting mixture was poured into aqueous 1 N HCl (50 mL). The aqueous layer was extracted with ethyl acetate (3×50 ml). The combined organic layers were washed with brine (25 mL), dried (MgSO$_4$), filtered and concentrated in vacuo. The crude residue was purified using silica gel column chromatography (3:1–2:1 hexane/ethyl acetate) to afford 0.357 g of a clear viscous oil (50% yield). An analytical sample was obtained by crystallization from ethyl acetate/hexane: mp 209–210° C.

$^1$H NMR (300 MHz, DMSO-d$_6$): δ 0.91 (21 H, s), 2.58 (2H, m), 3.63 (2H, m), 7.04 (1H, d, J=8.8), 7.06 (1H, s), 7.23 (1H, d, J=2.6), 7.40 (1H, J=8.7, 2.3), 7.51 (1H, d, J=8.6), 7.78 (1H, dd, J=8.6, 1.7), 9.92 (1H, s), 12.26 (1H, s); MS m/e 540 (MH$^+$).

Step B: 4-(5-Chloro-2-hydroxyphenyl)-1-methyl-3-(2-triisopropylsilyloxyethyl)-6-trifluoromethyl)-2(1H)-quinolinone (42, R$^3$=CF$_3$)

n-Butyl lithium (0.593 mL, 0.950 mmol, 2.1 equivalent, 1.6 M/hexane) was added to a stirred solution of the quinolinone 41 (0.244 g, 0.453 mmol) prepared in Step A, in THF at −78° C. After 15 minutes, neat iodomethane was added and the resulting mixture was allowed to warm to room temperature. After stirring for 12 hours, the reaction was quenched with aqueous 1 N HCl (10 mL) and poured into H$_2$O (50 mL). The aqueous layer was extracted with ethyl acetate (3×50 ml). The combined organic layers were washed with brine (25 mL), dried MgSO$_4$), filtered and concentrated in vacuo. The crude residue was purified using silica gel column chromatography (4:1–3:1 hexane/ethyl acetate) to afford 0.202 g of the title compound as a white solid (81% yield).

$^1$H NMR (300 MHz, DMSO-d$_6$): δ 0.92 (21 H, s), 2.63 (2H, m), 3.66 (2H, t, J=7.4), 3.75 (3H, s), 7.05 (1H, d, J=8.8), 7.15 (1H, s), 7.24 (1H, d, J=2.7), 7.41 (1H, dd, J=8.7, 2.6), 7.78 (1H, d, J=8.9), 7.91 (1H, dd, J=9.0, 1.9), 9.95 (1H, s).

Step C: 4-(5-Chloro-2-hydroxyphenyl)-1-methyl-3-(2-hydroxyethyl)-6-trifluoromethyl)-2(1H)-quinolinone (43, R$^3$=CF$_3$)

Tetrabutylammonium flouride (0.380 mL, 0.308 mmol, 2 equivalent, 1.0 M/THF) was added to a stirred solution of the quinolinone 42 (0.105 g, 0.190 mmol) prepared in Step B, in THF (10 mL). After 12 hours, the crude reaction mixture poured into H$_2$O (50 mL). The aqueous layer was extracted with ethyl acetate (3×50 ml). The combined organic layers were washed with brine (25 mL), dried (MgSO$_4$), filtered and concentrated in vacuo. The crude residue was purified using column chromatography (silica gel, 2.5% methanol/chloroform) to afford 74 mg of a white solid. The solid was recrystallized from ethyl acetate/hexane to provide 0.064 g (86% yield) of the title compound: mp 229–230° C.

¹H NMR (300 MHz, DMSO-d₆): δ 2.56 (2H, m), 3.40 (2H, m), 3.75 (3H, s), 4.57 (1H, m), 7.05 (1H, d, J=8.8), 7.14 (1H, s), 7.25 (1H, d, J=2.6), 7.41 (1H, dd, J=8.7, 2.7), 7.77 (1H, d, J=8.8), 7.89 (1H, dd, J=8.8, 2.0), 9.91 (1H, s); MS m/e 398 (MH⁺); Anal. Calcd. for $C_{19}H_{15}ClF_3NO_3$: C, 57.37; H, 3.80; N, 3.52. Found: C, 57.69; H, 3.88; N, 3.28.

EXAMPLE 45

4-(5-Chloro-2-methoxyphenyl)-1-methyl-3-(2-hydroxyethyl)-6-trifluoromethyl)-2(1H)-quinolinone (44, $R^3=CF_3$)

A mixture of the quinolinone 42 prepared in Example 44, Step B (0.202 g, 0.365 mmol), dimethylsulfate (0.038 mL, 0.402 mmol, 1.1 equivalent), and potassium carbonate (0.056 g, 0.402 mmol, 1.1 equivalent) in acetone (15 mL) was heated at reflux for 3 hours. The resulting mixture was poured into H₂O (25 mL). The aqueous layer was extracted with ethyl acetate (3×50 ml). The combined organic layers were washed with brine (25 mL), dried (MgSO₄), filtered and concentrated in vacuo. The crude quinolinone (0.228 g) was used in the subsequent reaction without purification or characterization.

Tetrabutylammonium flouride (0.802 mL, 0.802 mmol, 2 equivalent, 1.0 MITHF) was added to a stirred solution of the quinolinone prepared above (0.228 g, 0.401 mmol) in THF (10 mL). After 12 hours, the crude reaction mixture was poured into H₂O (50 mL). The aqueous layer was extracted with ethyl acetate (3×50 ml). The combined organic layers were washed with brine (25 mL), dried (MgSO₄), filtered and concentrated in vacuo. The crude residue was purified using column chromatography (silica gel, 1:1–1:2 hexane/ethyl acetate) to afford 0.148 g of a white solid. The solid was recrystallized from ethyl acetate/hexane to provide 0.139 g (84% yield) of the title compound: mp 175–176° C.

¹H NMR (300 MHz, DMSO-d₆): δ 2.48 (2H, m), 3.37 (2H, m), 3.67 (3H, s), 3.75 (3H, s), 4.57 (1 H, t, 5.4), 7.06 (1H, s), 7.29 (1H, d, J=9.0), 7.35 (1H, d, J=1.3), 7.61 (1H, dd, J=8.8, 2.7), 7.77 (1H, d, J=8.8), 7.89 (1H, dd, J=8.8, 1.9); MS m/e 412 (MH⁺); Anal. Calcd. for $C_{20}H_{17}ClF_3NO_3$: C, 58.33; H, 4.16; N, 3.40. Found: C, 58.30; H, 4.07; N, 3.18.

EXAMPLE 46

4-(5-Chloro-2-methoxyphenyl)-3-methyl-6-trifluoromethyl-2(1H)-quinolinone

A solution of compound 33 ($R^3=CF_3$, $R^8=H$, n=1) (5.63 mmol), 33% HBr in AcOH (38.3 mmol) and 10 mL of AcOH was heated to 75° C. for 3 hours. The solution was cooled to room temperature and quenched with H₂O (50 mL) and then agitated for 12 hours. The precipitate was filtered, washed with H₂O, and dried in vacuo. The pale brown solid was recrystallized from ethyl acetate/hexane. The title compound was isolated as a white solid (0.550 g, 27% yield).

¹H NMR (300 MHz, CDCl₃): δ 2.04 (s, 3H), 3.72 (s, 3H), 7.03 (d, 1H, J=9.0 Hz), 7.12 (s, 1H), 7.44 (m, 3H), 7.65 (d, 1H, J=8.4 Hz), 10.93 (br s, 1H); MS m/e 368 (MH⁺); Anal. Calcd. for $C_{18}H_{13}ClF_3NO_2 \cdot 0.33 H_2O$: C, 58.79; H, 3.56; N, 3.81. Found: C, 58.89; H, 3.82; N, 3.53.

EXAMPLE 47

4-(5-Chloro-2-hydroxyphenyl)-3-(2-hydroxyethyl)-6-(trifluoromethyl)-2(1H)-quinolinone (31a, $R^3=CF_3$, n=2)

Step A: 3-(2-Hydroxyethyl)-4-hydroxy-6-chlorocoumarin (45)

To a solution of γ-butyrolactone (15.5 g, 178.0 mmol) in THF (100 mL) at −78° C. was added a 1.0 M THF solution of LiHMDS (356 mL, 356 mmol), and the resulting mixture stirred at −78° C. for 1.5 hours. A solution of 5-chlorosalicylic methyl ester (16.6 g, 98% purity, 89.0 mmol) in THF (95 mL) was added. After stirring for 1 hour at 0° C., the mixture was warmed to room temperature overnight to ensure complete reaction. After cooling to 0° C., conc. HCl (12 N, 150 mL) was slowly added to bring the pH to 1. The reaction solution was stirred until HPLC analysis indicated the absence of the keto-ester intermediate. To the mixture was added 400 mL CH₂Cl₂ and 300 mL H₂O; the organic phase was separated and the aqueous layer was extracted with CH₂Cl₂ (100 mL). The organic layers were combined and dried over anhydrous Na₂SO₄, and the solvent was removed under reduced pressure to give a solid. Heptane (165 mL) was added to a solution of the solid in THF (290 mL) to crystallize the product. After cooling to 0–5° C. for about 3 hours, the product was isolated by filtration and washed with heptane. After drying in vacuo, a total of 13.9 g (66% yield) of the title compound as off-white crystals was obtained. m.p. 185–186° C.; MS m/z 240;

¹H NMR (DMSO, 300 MHz) δ 7.84 (d, 1H, J=2.4 Hz), 7.61 (dd, 1H, J=2.4, 8.8 Hz), 7.38 (d, 1H, J=8.8 Hz), 3.56 (t, 2H, J=6.6 Hz), 2.73 (t, 2H, J=6.6 Hz); ¹³C NMR (DMSO, 75 MHz) δ 162.6, 159.9, 150.5, 131.4, 127.9, 122.4, 118.2, 117.8, 103.2, 59.4, 27.6; IR (cm⁻¹) 3247.2, 2945.1, 2458.6, 1664.9, 1623.9, 1572.7, 1311.5, 1378.1, 1070.8, 825.0.

Step B: 2,3-Dihydro-8-chloro-4H-furobenzopyran-4-one (46)

To a solution of 3-(2-hydroxyethyl)-4-hydroxy-6-chlorocoumarin (45) (8 g, 33.3 mmol) in toluene (360 mL) at room temperature was added p-TSA (0.95 g, 5.0 mmol), and the resulting solution was refluxed with the removal of water using a Dean-Stark condenser. The reaction mixture was cooled to room temperature and washed with saturated sodium bicarbonate solution twice. Toluene was removed by atmospheric distillation to a final volume of 32 mL. After cooling to 70° C., the product started to crystallize. The crystal slurry was held between 55–65° C. for 30 minutes, followed by cooling to 0–5° C. The product was isolated by filtration, washed with cold toluene, and dried in vacuo. A total of 5.5 g (74% yield) of the title compound as off-white crystals was obtained. m.p. 144–146° C.; MS m/z 223 (M+H);

¹H NMR (CDCl₃, 300 MHz) δ 7.58 (d, 1H, J=2.5 Hz), 7.49 (dd, 1H, J=2.3, 8.8 Hz), 7.30 (d, 1H, J=8.9 Hz), 4.90 (t, 2H, J=9.3 Hz), 3.21 (t, 2H, J=9.5 Hz); ¹³C NMR (CDCl₃, 75 MHz) δ 166.4, 160.3, 153.4, 132.6, 129.6, 122.4, 118.6, 113.8, 103.6, 74.9, 27.1; IR (cm⁻¹) 3073.1, 2975.8, 1721.2, 1644.4, 1490.8, 1403.7, 1270.6, 1111.8, 1040.1.

Step C: 4-(4'-Trifluoromethylphenylcarboxamide)-5-(2-hydroxy-5-chloro)-2,3-dihydrofuran (47)

To a solution of 2,3-dihydro-8-chloro-4H-furobenzopyran-4-one (46) (1.02 g, 4.58 mmol) and 4-(trifluoromethyl)aniline (0.74 g, 4.58 mmol) in THF (50 mL) at −15° C. was added LiHMDS (10.5 mL, 10.5 mmol, 1.0M solution in THF). The clear, red solution was stirred at −15° C. until HPLC analysis indicated <1% of compound (46) remained (approximately 30 minutes). The reaction mixture was quenched by the addition of an aqueous solution of NaH₂PO₄ (50 mL, 10 wt % in H₂O). After the addition of MTBE (25 mL), the layers were separated and the rich organic phase washed successively with NaH₂PO₄ (50 mL, 10 wt % in H₂O) and saturated brine solution. After drying over Na₂SO₄, the solution was concentrated to give the title compound as a clear, orange oil (1.76 g, 100% yield) which crystallized upon refrigeration. Addition of dichloromethane (20 mL) gave white crystals, which were isolated by filtration, washed with dichloromethane (10 mL) and dried to give 1.6 grams of the title compound (90% yield). m.p 180–180.5° C.; MS m/z 384 (M+H);

$^1$H NMR (DMSO, 300 MHz) δ 9.76 (s, 1H), 9.34 (s, 1H), 7.76 (d, 2H, J=8.5 Hz), 7.60 (d, 2H, J=8.7 Hz), 7.26 (s, 1H), 7.24 (dd, 1 H, J=2.2, 7.0 Hz), 6.83 (dd, 1H, J=2.4,7.1), 4.52 (t, 2H, J=9.6 Hz), 3.16 (t, 2H, J=9.6 Hz); $^{13}$C NMR (DMSO, 75 MHz) δ 165.5, 159.7, 155.9, 144.7, 132.0, 131.3, 127.3, 123.7, 121.7, 121.2, 119.5, 110.1, 71.5, 32.9; IR (cm$^{-1}$) 3303.6, 2950.2, 1654.6, 1608.5, 1531.7, 1408.8, 1326.9, 1116.9, 1065.7, 840.4.

Step D: 4-(5-Chloro-2-hydroxyphenyl)-3-(2-hydroxyethyl)-6-(trifluoromethyl)-2(1H)-quinolinone (31a, R³=CF₃, n=2)

A solution of 4-(4'-trifluoromethylphenylcarboxamide)-5-(2-hydroxy-5-chloro)-2,3-dihydrofuran (47) prepared in Step C (1.76 g, 4.58 mmol) in MeOH (500 mL) was purged with nitrogen and irradiated with a 450 W Hanovia lamp at 30–40° C. until HPLC analysis indicated <1% of compound (47) remained. The MeOH was then concentrated in vacuo, and the resulting oil dissolved in dichloromethane (50 mL). Crystals formed after stirring for one hour at room temperature. After cooling the slurry to 0° C., the crystals were isolated by filtration and dried. A total of 0.54 g (30% yield) of the title compound was obtained as a crystalline solid with an HPLC purity of 97 area % and had physical characterizing data which was identical to the compound of Example 20.

What is claimed is:

1. A compound of the formula

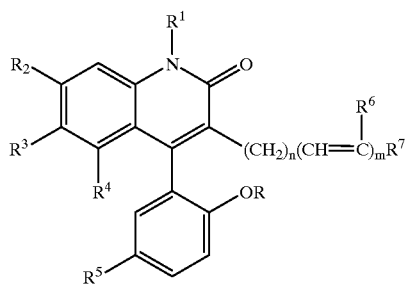

I wherein

R and R¹ each are independently hydrogen or methyl;

R², R³ and R⁴ each are independently hydrogen, halogen, nitro or trifluoromethyl, provided R², R³, and R⁴ are not all hydrogen;

R⁵ is bromo, chloro or nitro;

R⁶ is hydrogen or fluoro;

n is an integer from 0 to 6;

m is an integer of 0 or 1; and

R⁷ is CH₃, —CRR¹OH, —CHO, —C=NOH, —COCH₃ or aryl optionally substituted by one or two substituents selected from the group consisting of halogen, hydroxy, methoxy, amino, acetylamino and trifluoromethyl;

or a nontoxic pharmaceutically acceptable salt thereof.

2. The compound of claim 1 having the formula

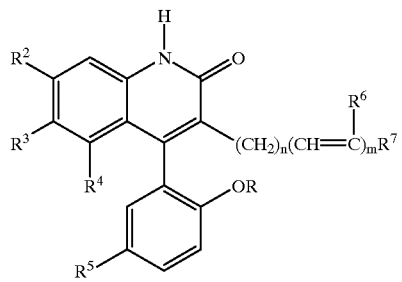

wherein

R is hydrogen or methyl;

R², R³ and R⁴ each are independently hydrogen, halogen, nitro or trifluoromethyl, provided R², R³, and R⁴ are not all hydrogen;

R⁵ is chloro;

R⁶ is hydrogen or fluoro;

n is an integer from 0 to 3;

m is an integer of 0 or 1; and

R⁷ is —CH₂OH, —CHO, —C=NOH, or aryl optionally substituted by one or two substituents selected from the group consisting of halogen, hydroxy, methoxy, amino, acetylamino and trifluoromethyl;

or a nontoxic pharmaceutically acceptable salt thereof.

3. The compound of the claim 2 wherein R³ is trifluoromethyl, R² and R⁴ are hydrogen, and R⁷ is —CH₂OH; or a nontoxic pharmaceutically acceptable salt thereof.

4. The compound of claim 2 wherein R³ is trifluoromethyl, R² and R⁴ are hydrogen, and R⁷ is aryl optionally substituted by one or two substituents selected from the group consisting of halogen, hydroxy, methoxy, amino, acetylamino and trifluoromethyl; or a nontoxic pharmaceutically acceptable salt thereof.

5. The compound of claim 1 selected from the group consisting of:

4-(5-chloro-2-methoxyphenyl)-3-(hydroxymethyl)-6-(trifluoromethyl)-2(1H)-quinolinone;

4-(5-chloro-2-methoxyphenyl)-3-(hydroxymethyl)-7-(trifluoromethyl)-2(1H)-quinolinone;

4-(5-chloro-2-methoxyphenyl)-1,2-dihydro-2-oxo-6-(trifluoromethyl)-3-quinolinecarboxaldehyde;

4-(5-chloro-2-methoxyphenyl)-3-(3-hydroxy-1-propenyl)-6-(trifluoromethyl)-2(1H)-quinolinone;

4-(5-chloro-2-methoxyphenyl)-3-(3-hydroxypropyl)-6-(trifluoromethyl)-2(1H)-quinolinone;

4-(5-chloro-2-hydroxyphenyl)-3-(hydroxymethyl)-6-(trifluoromethyl)-2(1H)-quinolinone;

4-(5-chloro-2-hydroxyphenyl)-3-(3-hydroxy-1-propenyl)-6-(trifluoromethyl)-2(1H)-quinolinone;

4-(5-chloro-2-hydroxyphenyl)-3-(3-hydroxypropyl)-6-(trifluoromethyl)-2(1H)-quinolinone;

(E)-4-(5-cholro-2-hydroxyphenyl)-3-(2-fluoro-3-hydroxy-1-propenyl)-6-trifluoromethyl)-2(1H)-quinolinone;

(Z)-4-(5-chloro-2-hydroxyphenyl)-3-(2-fluoro-3-hydroxy-1-propenyl)-6-(trifluoromethyl)-2(1H)-quinolinone;

(E)-4-(5-chloro-2-methoxyphenyl)-3-(2-fluoro-3-hydroxy-1-propenyl)-6-(trifluoromethyl)-2(1H)-quinolinone;

(Z)-4-(5-chloro-2-methoxyphenyl)-3-(2-fluoro-3-hydroxy-1-propenyl)-6-(trifluoromethyl)-2(1H)-quinolinone;

4-(5-chloro-2-hydroxyphenyl)-3-(2-hydroxyethyl)-6-(trifluoromethyl)-2(1H)-quinolinone;

4-(5-chloro-2-methoxyphenyl)-3-(2-hydroxyethyl)-6-trifluoromethyl-2(1H)-quinolinone;

4-(5-chloro-2-methoxyphenyl)-3-(4-methoxyphenyl)-6-(trifluoromethyl)-2(1H)-quinolinone;

4-(5-chloro-2-methoxyphenyl)-3-[(4-methoxyphenyl)methyl]-6-(trifluoromethyl)-2(1H)-quinolinone;

4-(5-chloro-2-methoxyphenyl)-3-(4-nitrophenyl)-6-(trifluoromethyl)-2(1H)-quinolinone;

4-(5-chloro-2-methoxyphenyl)-3-(4-aminophenyl)-6-(trifluoromethyl)-2(1H)-quinolinone;

4-(5-chloro-2-hydroxyphenyl)-3-(3,4-dimethoxyphenyl)-6-(trifluoromethyl)-2(1H)-quinolinone;

4-(5-chloro-2-hydroxyphenyl)-3-(2,4-dihydroxyphenyl)-6-(trifluoromethyl)-2(1H)-quinolinone;

4-(5-chloro-2-hydroxyphenyl)-3-(4-hydroxyphenyl)-6-(trifluoromethyl)-2(1H)-quinolinone;

4-(5-chloro-2-hydroxyphenyl)-3-[(4-hydroxyphenyl)methyl]-6-(trifluoromethyl)-2(1H)-quinolinone;

4-(5-chloro-2-hydroxyphenyl)-3-(4-acetamidophenyl)-6-(trifluoromethyl)-2(1H)-quinolinone;

4-(5-chloro-2-hydroxyphenyl)-3-(4-aminophenyl)-6-(trifluoromethyl)-2(1H)-quinolinone;

4-(5-chloro-2-hydroxyphenyl)-3-[2-(4-hydroxyphenyl)ethyl]-6-(trifluoromethyl)-2(1H)-quinolinone;

4-(5-chloro-2-hydroxyphenyl)-3-methyl-6-(trifluoromethyl)-2(1H)-quinolinone;

4-[4-(5-chloro-2-hydroxyphenyl)-1,2-dihydro-2-oxo-6-(trifluoromethyl)quinolin-3-yl]-3-buten-2-one;

4-(5-chloro-2-hydroxyphenyl)-1,2-dihydro-2-oxo-6-(trifluoromethyl)-3-quinolinecarboxaldehyde oxime;

4-(5-chloro-2-methoxyphenyl)-1,2-dihydro-2-oxo-6-(trifluoromethyl)-3-quinolinecarboxaldehyde oxime; and 4-(5-chloro-2-hydroxyphenyl)-3-(2-hydroxy-2-methylpropyl)-6-(trifluoromethyl)-2(1H)-quinolinone;

or a nontoxic pharmaceutically acceptable salt thereof.

6. The compound of claim 5 selected from the group consisting of:

4-(5-chloro-2-methoxyphenyl)-3-(3-hydroxy-1-propenyl)-6-(trifluoromethyl)-2(1H)-quinolinone;

4-(5-chloro-2-methoxyphenyl)-3-(3-hydroxypropyl)-6-(trifluoromethyl)-(1H)-quinolinone;

4-(5-chloro-2-hydroxyphenyl)-3-(hydroxymethyl)-6-(trifluoromethyl)-2(1H)-quinolinone;

4-(5-chloro-2-hydroxyphenyl)-3-(3-hydroxy-1-propenyl)-6-(trifluoromethyl)-2(1H)-quinolinone;

4-(5-cholro-2-hydroxyphenyl)-3-(3-hydroxypropyl)-6-(trifluoromethyl)-2(1H)-quinolinone;

4-(5-chloro-2-hydroxyphenyl)-3-(2-hydroxyethyl)-6-(trifluoromethyl)-2(1H)-quinolinone;

4-(5-chloro-2-methoxyphenyl)-3-(2-hydroxyethyl)-6-trifluoromethyl-2(1H)-quinolinone;

4-(5-chloro-2-hydroxyphenyl)-3-(4-hydroxyphenyl)-6-(trifluoromethyl)-2(1H)-quinolinone;

4-(5-chloro-2-hydroxyphenyl)-3-[(4-hydroxyphenyl)methyl]-6-(trifluoromethyl)-2(1H)-quinolinone; and 4-(5-chloro-2-hydroxyphenyl)-3-(4-aminophenyl)-6-(trifluoromethyl)-2(1H)-quinolinone;

or a nontoxic pharmaceutically acceptable salt thereof.

7. The compound of claim 1 which is 4-(5-chloro-2-hydroxyphenyl)-3-(2-hydroxyethyl)-6-(trifluoromethyl)-2(1H)-quinolinone.

8. The compound of claim 1 which is 4-(5-chloro-2-methoxyphenyl)-3-(2-hydroxyethyl)-6-trifluoromethyl-2(1H)-quinolinone.

9. A pharmaceutical composition for the treatment of disorders responsive to openers of the large conductance calcium-activated potassium channels comprising a therapeutically effective amount of a compound as defined in claim 1 in association with a pharmaceutically acceptable carrier or diluent.

10. A method for the treatment of disorders responsive to opening of the large conductance calcium-activated potassium channels in a mammal in need thereof, which comprises administering to said mammal a therapeutically effective amount of a compound as defined in claim 1.

11. The method of claim 10 wherein said disorder is ischemia, stroke, convulsions, epilepsy, asthma, irritable bowel syndrome, migraine, traumatic brain injury, spinal cord injury, sexual dysfunction and urinary incontinence.

12. The method of claim 10 wherein said disorder is male erectile dysfunction.

13. The method of claim 11 wherein said disorder is stroke or traumatic brain injury.

14. The method of claim 11 wherein said disorder is sexual dysfunction.

* * * * *